«12» United States Patent
Bacich et al.

[11] Patent Number: 5,810,776
[45] Date of Patent: *Sep. 22, 1998

[54] METHOD AND APPARATUS FOR PERFORMING LAPAROSCOPY

[75] Inventors: Steven R. Bacich, Laguna Niguel; John P. Greelis, Aliso Viejo; Hien Nguyen, Santa Ana; Tuoc Nguyen, Westminster, all of Calif.

[73] Assignee: Imagyn Medical, Inc., Laguna Niguel, Calif.

[*] Notice: This patent issued on a continued prosecution application filed under 37 CFR 1.53(d), and is subject to the twenty year patent term provisions of 35 U.S.C. 154(a)(2).

[21] Appl. No.: 600,422

[22] Filed: Feb. 13, 1996

[51] Int. Cl.⁶ ................................... A61M 37/00
[52] U.S. Cl. ........................................ 604/131
[58] Field of Search ................ 604/164, 96, 104, 604/171, 173, 280

[56] References Cited

U.S. PATENT DOCUMENTS

| | | |
|---|---|---|
| 2,548,602 | 4/1951 | Greenburg . |
| 3,789,852 | 2/1974 | Kim . |
| 4,141,364 | 2/1979 | Schultze . |
| 4,211,234 | 7/1980 | Fisher . |
| 4,350,147 | 9/1982 | Sarrine . |
| 4,406,656 | 9/1983 | Hattler et al. . |
| 4,601,713 | 7/1986 | Fugua .................... 604/280 |
| 4,646,722 | 3/1987 | Silverstein et al. . |
| 4,721,097 | 1/1988 | D'Amelio . |
| 4,738,666 | 4/1988 | Fugua .................... 604/280 |
| 4,798,193 | 1/1989 | Giesy ..................... 604/164 |
| 4,800,870 | 1/1989 | Reid, Jr. . |
| 4,928,669 | 5/1990 | Sullivan . |
| 5,025,778 | 6/1991 | Silverstein et al. . |
| 5,106,368 | 4/1992 | Uldall et al. . |
| 5,201,908 | 4/1993 | Jones . |
| 5,213,092 | 5/1993 | Uram . |
| 5,217,001 | 6/1993 | Nakao et al. . |
| 5,232,446 | 8/1993 | Avney .................... 604/96 |
| 5,318,588 | 6/1994 | Horzewski et al. . |
| 5,334,167 | 8/1994 | Cocanower . |
| 5,378,230 | 1/1995 | Mahurkar . |
| 5,386,817 | 2/1995 | Jones . |
| 5,413,560 | 5/1995 | Solar .................... 604/164 |
| 5,503,616 | 4/1996 | Jones . |
| 5,573,508 | 11/1996 | Thornton . |

*Primary Examiner*—Manuel Mendez
*Attorney, Agent, or Firm*—Knobbe, Martens, Olson & Bear, LLP

[57] ABSTRACT

A laparoscopic introducer and method of use comprise a laparoscopic channel and a guide channel for a secondary instrument. Upon initial insertion of the introducer, the guide channel closely conforms to the body of the introducer so as to only negligibly increase the cross-sectional profile thereof. Following insertion, the guide channel can be distended by means of a dilator. Thus, the guide channel allows a secondary instrument to be inserted into the body to perform laparoscopic procedures wherein the instrument is inserted and utilized along the same longitudinal axis as the laparoscope. Thus, the number of laparoscopic ports are reduced and visual distortions associated with triangulation are avoided. The guide channel is constructed from an extremely thin, but very strong and noncompliant membrane which may also be reinforced by means of a force distribution mechanism. The guide channel may also be provided with guide rails or other tracking mechanisms to ensure accurate and secure advancement of the dilator or secondary instrument. The method of construction of the introducer and an apparatus and method for dilation are also disclosed.

30 Claims, 12 Drawing Sheets

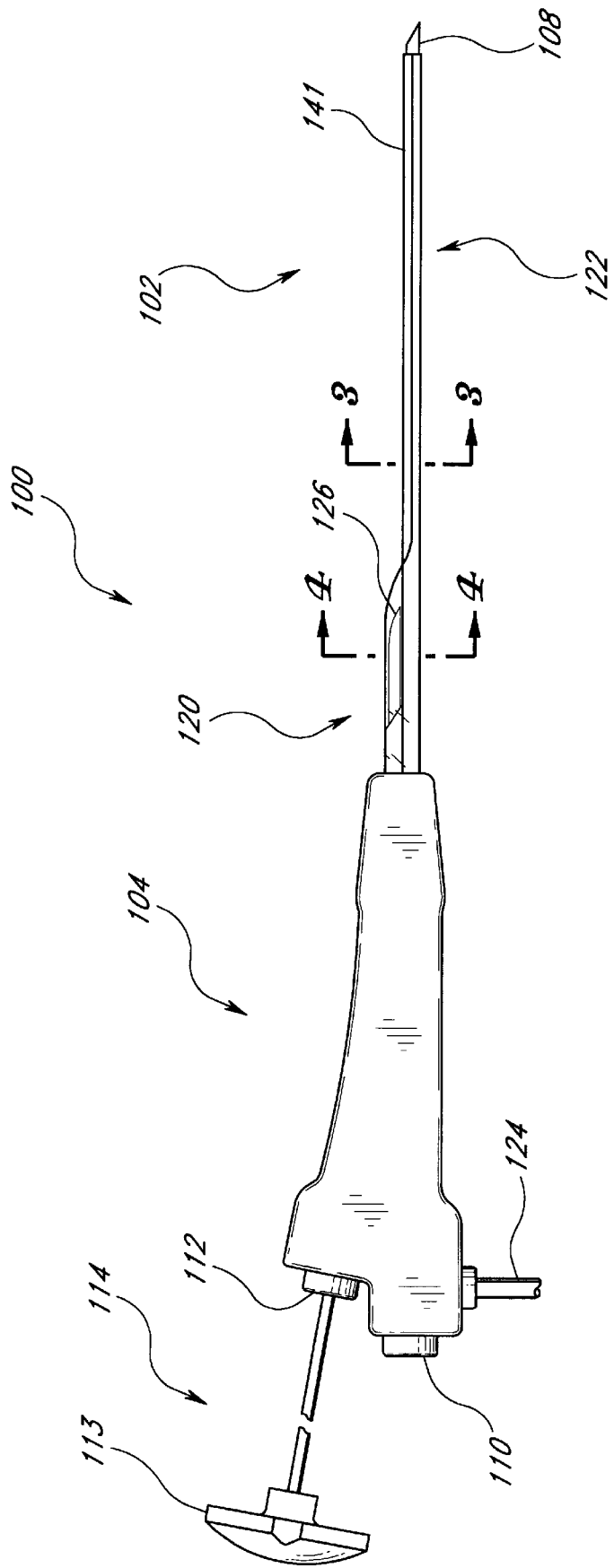

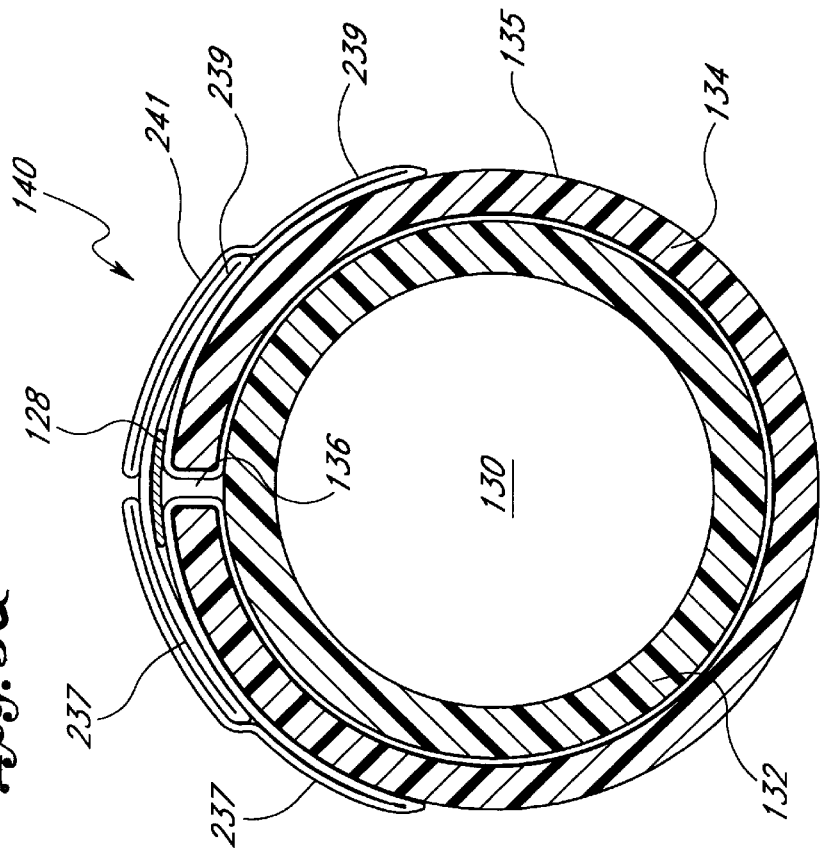
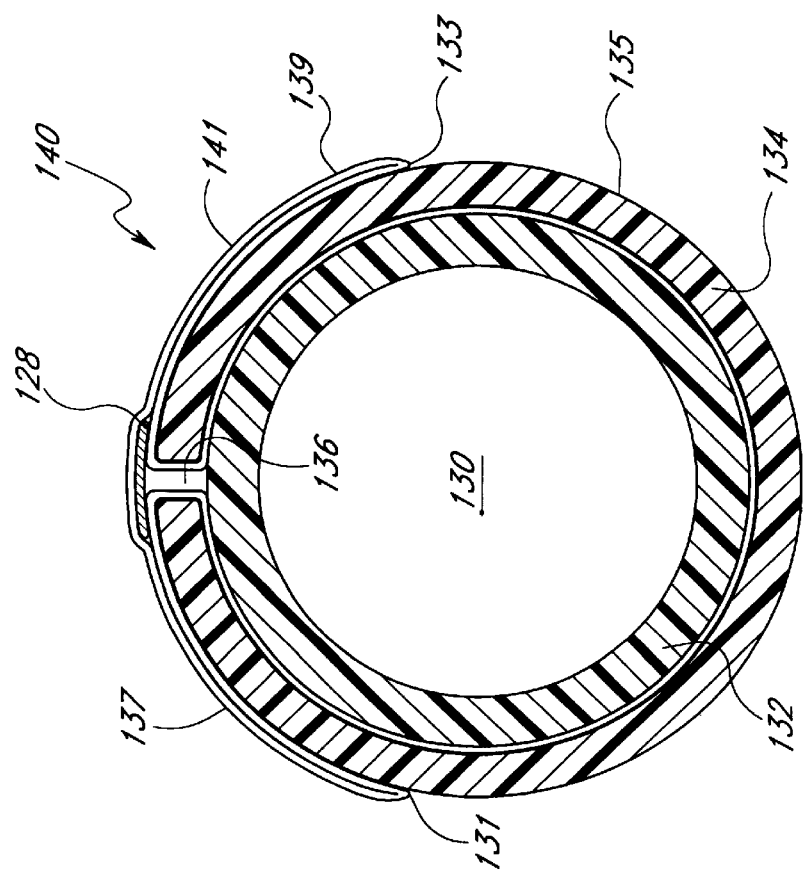

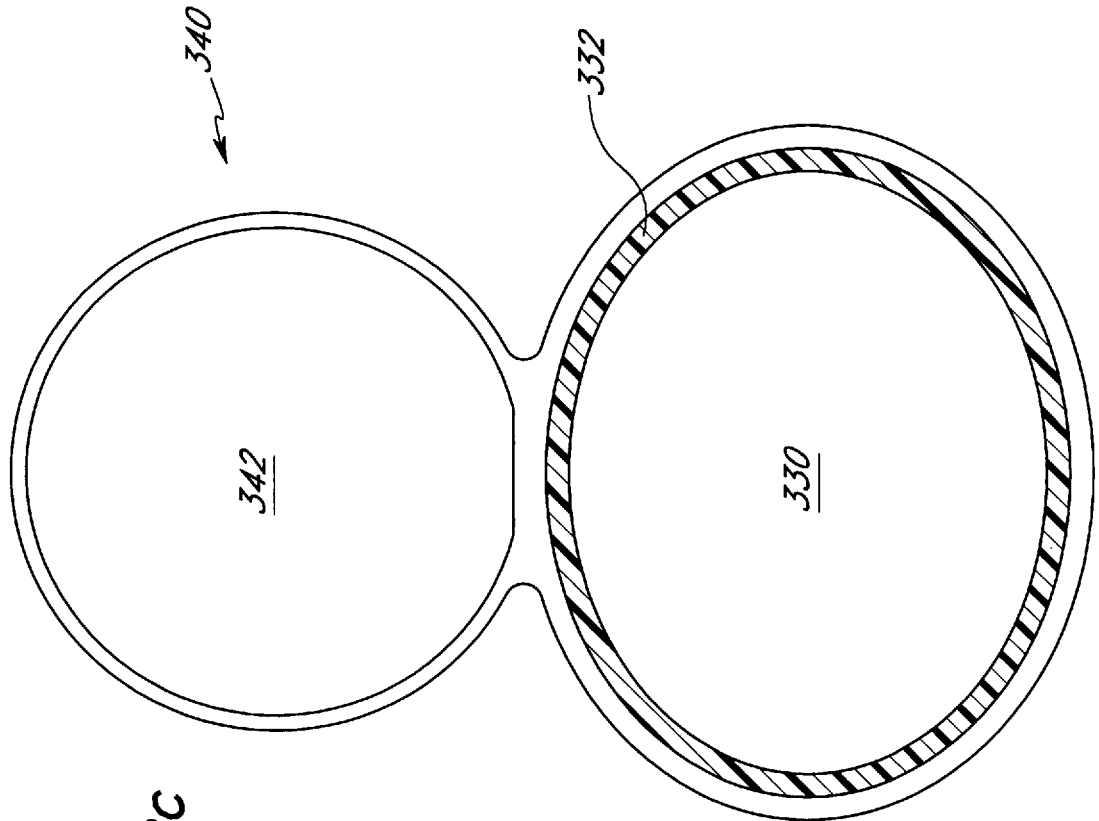
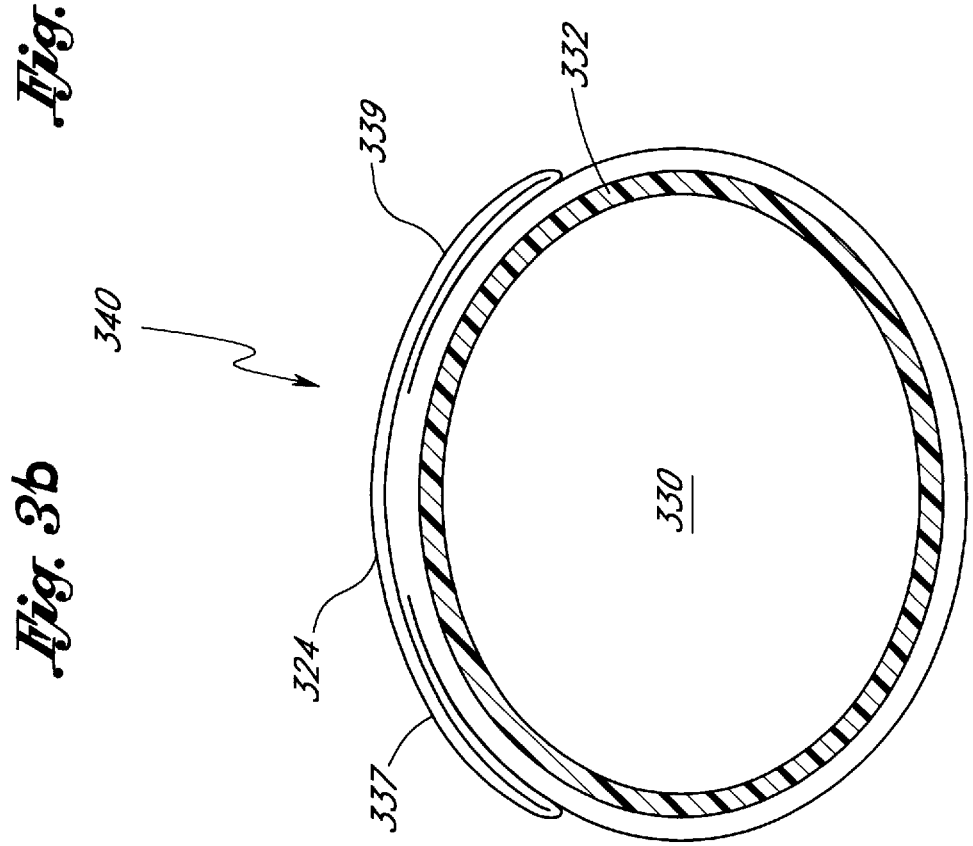
Fig. 3b
Fig. 3c

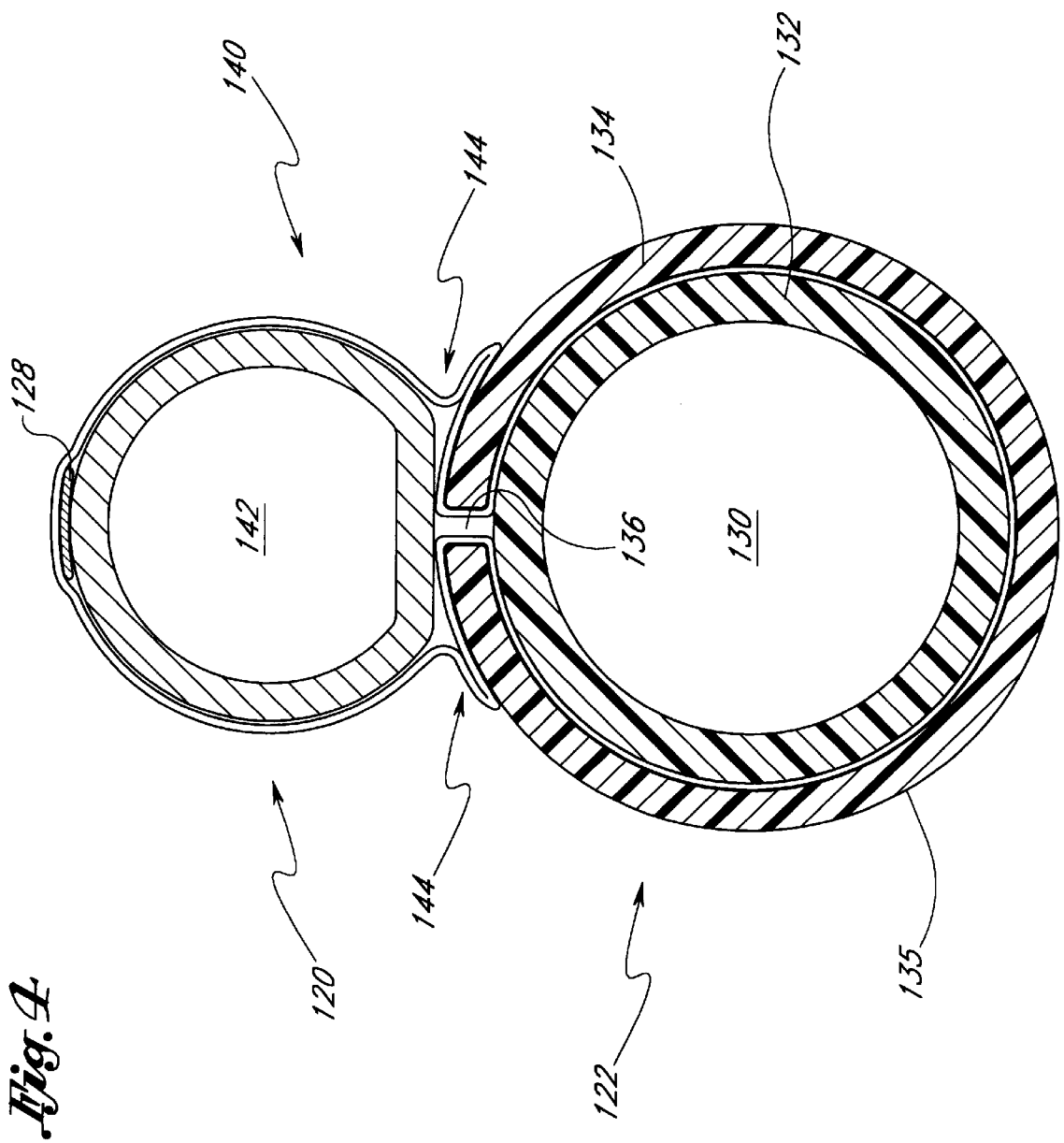

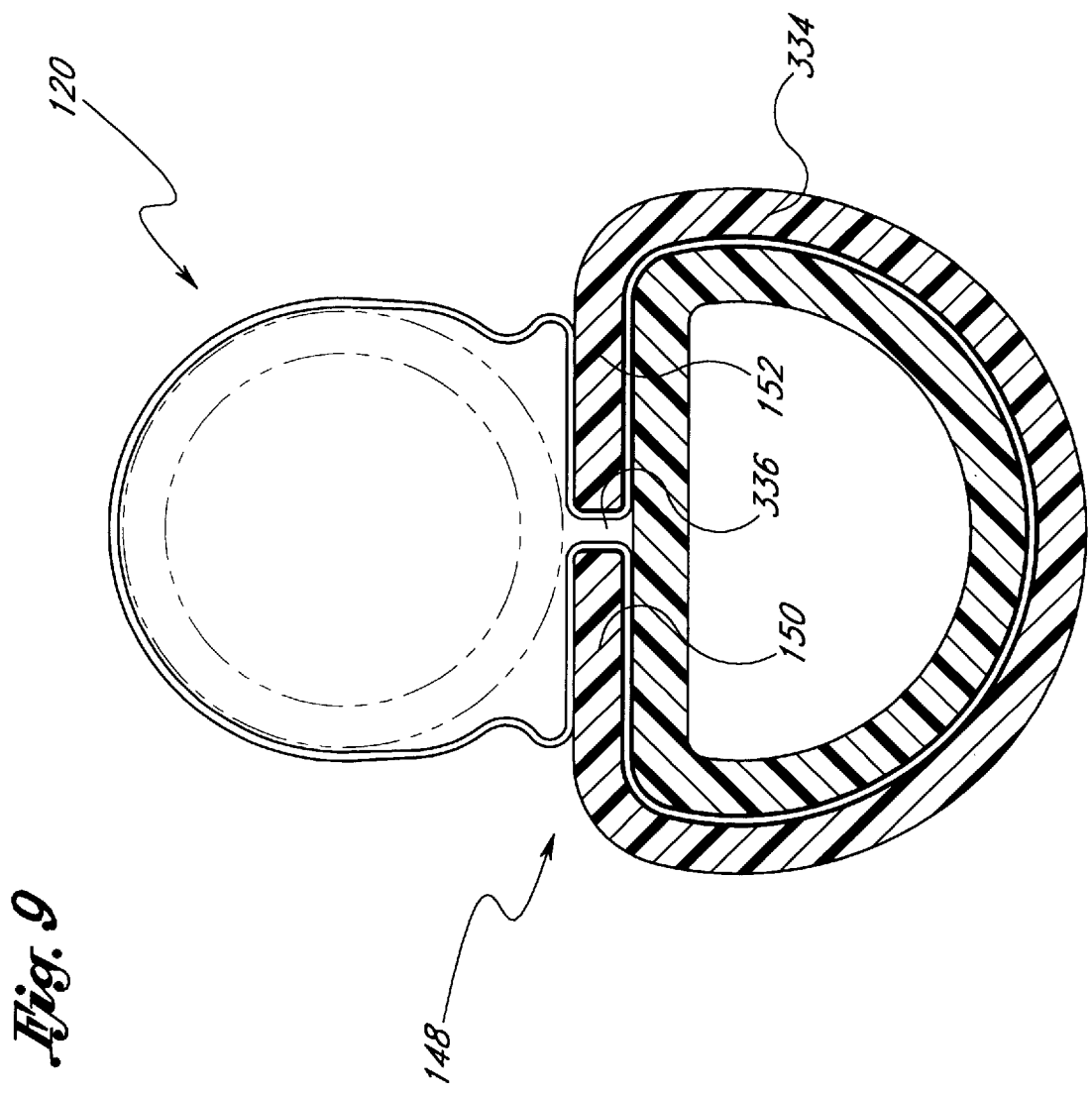

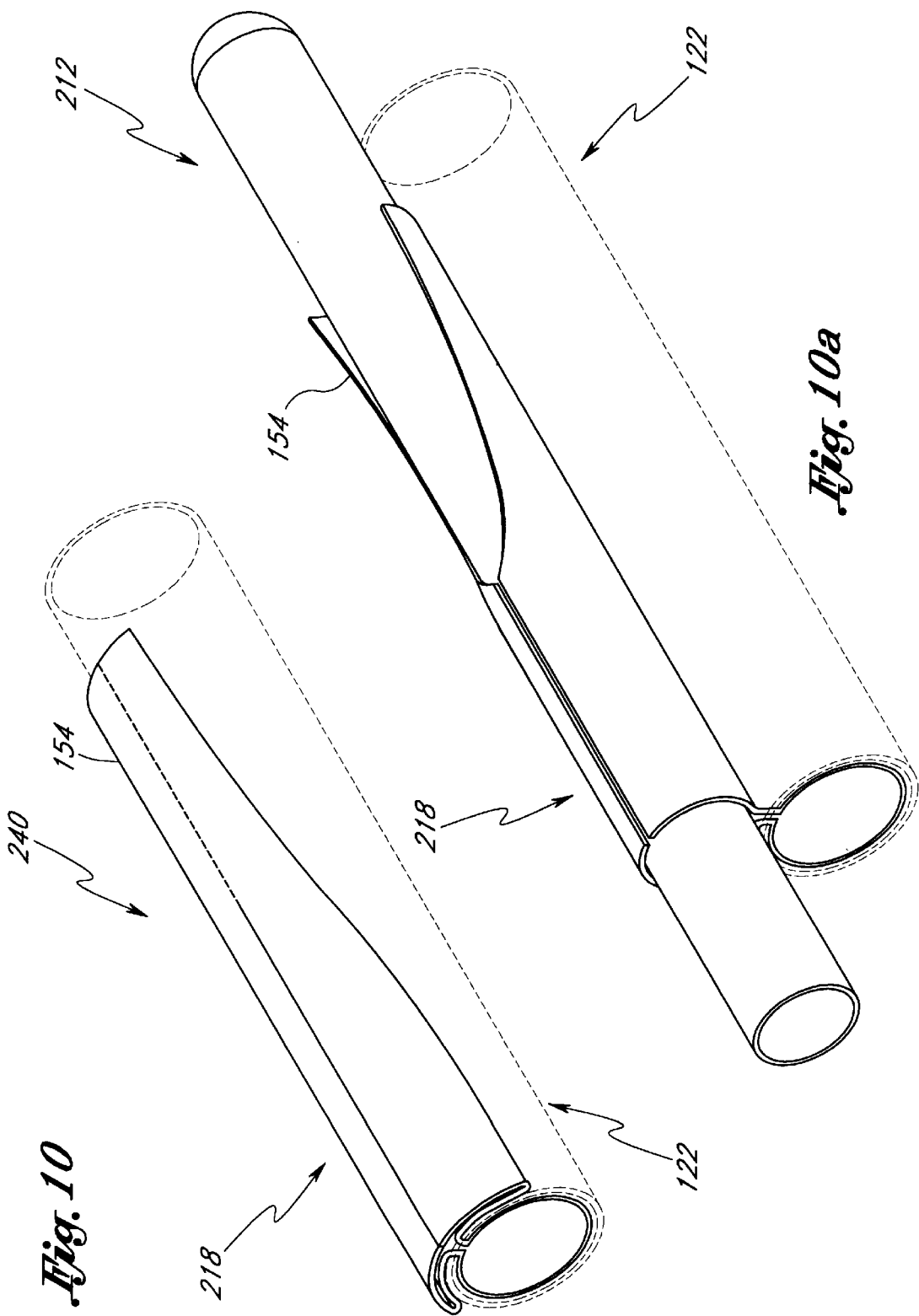

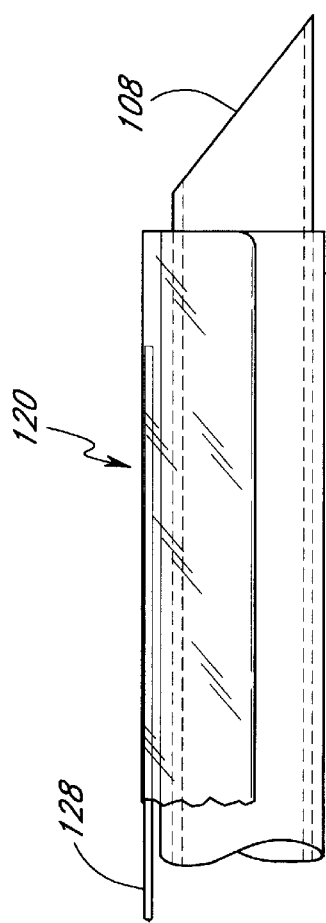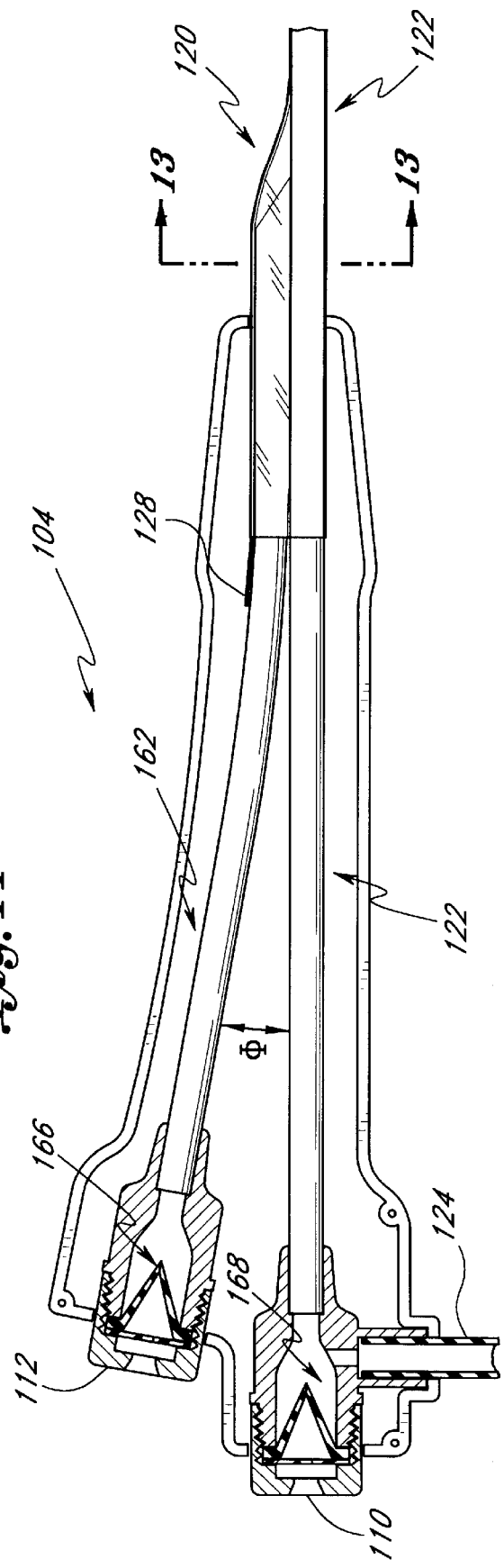
Fig. 11
Fig. 12

METHOD AND APPARATUS FOR PERFORMING LAPAROSCOPY

FIELD OF THE INVENTION

The present invention relates to a method and apparatus for performing laparoscopy, and more particularly to a laparoscopic surgical access device or introducer providing a guide channel for the insertion of a secondary instrument into the patient's body, and to a method of constructing and using such introducer to reduce the pain, discomfort, and cost associated with laparoscopic procedures.

BACKGROUND OF THE INVENTION

Laparoscopy encompasses a number of surgical procedures in which an endoscope (or, when used in laparoscopy, a "laparoscope") is used to examine the abdominal cavity or peritoneal cavity. Typically, in addition to such examination, other diagnostic or surgical procedures are performed upon the patient with the benefit of visualization achieved through the laparoscope. The laparoscope typically achieves access to the interior of the body through a small incision or "port" formed therein. Frequently, two or more ports are necessary in order to accomplish the diagnostic or surgical laparoscopic procedure. For example, in a typical laparoscopic cholecystectomy, as many as four to six ports must be made in the patient's body in order to accommodate the various endoscopic instruments necessary to complete this procedure. Obviously, other types of laparoscopic procedures will require more or fewer of ports.

Laparoscopes of the type used in such procedures are typically rigid rod lens-type systems, having a diameter of usually 10 mm or sometimes 12 mm. Although laparoscopy has been attempted with laparoscopes of smaller diameters, such as 5 or 7 mm, such procedures have suffered due to poor visual qualities. Thus, a 10-mm diameter laparoscope remains the endoscope of choice.

Because of its relatively large cross-sectional profile, in order to form a port for the laparoscope, large trocars and sleeves are required to gain entry into the peritoneal cavity or abdomen. The sleeve is a type of cannula or other surgical access device through which the laparoscope or other surgical instruments may be inserted into the body. For this reason, the sleeve is also sometimes referred to as a "sheath" or "introducer." However, because of the girth of the trocar and associated sleeve, the overall cross-sectional profile of the system is substantial. Thus, tremendous force is sometimes required in order to penetrate the outer skin, layers of fat and fascia, and possibly the peritoneum in order to gain entry into the abdominal cavity. On occasion the vital organs lying within the cavity have been injured by the sharp tip of the trocar as it penetrates the very tough and elastic peritoneum.

Although present laparoscopic procedures represent a marked improvement over traditional open-field surgery, they still suffer from a number of disadvantages. For example, as noted above, visceral injury can result from the establishment of the laparoscopic ports. Second, such procedures still require the use of a general anesthesia within the security of hospital operating rooms. Moreover, following the procedure, the patient still suffers from a certain amount of pain and discomfort, although recovery times have been vastly reduced through endoscopic procedures of this type. Nevertheless, there remains a need to reduce the cost and patient discomfort associated with these types of procedures.

Thus, one goal of present laparoscopic practitioners is to reduce the profile of the instruments necessary to form a port in the patient's body. Smaller ports will result in the use of smaller profile instruments with the attendant reduced risk of injury and pain to the patient. Another goal of practitioners is to reduce the number of ports necessary to accomplish a particular procedure. Presently, since a laparoscope is inserted through one port, the surgical instruments necessary to accomplish the procedure must be inserted through one or more remote ports and visualized within the body by means of the laparoscope. This visualization process is sometimes referred to as "triangulation." Although it has been effective, triangulation results in certain types of visual distortions, which limits laparoscopy to only very skilled and experienced practitioners.

Accordingly, the prior art is familiar with the advantages of inserting a surgical instrument through an extra port which is incorporated into the body of an endoscope in order to reduce the total number of ports. In this regard, attempts have also been made to provide a endoscopic sheath with secondary or auxiliary channels which are expandable after insertion. In other words, the prior technology includes endoscopes or endoscopic sheaths which can be inserted through openings in the body which are just large enough to admit entrance of the endoscope. Once inside the body, however, the secondary or auxiliary channel can be dilated in order to permit the entrance of a secondary instrument. Hopefully, this is accomplished without significantly increasing pain or discomfort to the patient, thereby allowing the procedure to be performed under only a local anesthetic and on an out-patient basis. Thus, if patient pain is not minimized, general anesthesia is required anyway, and no advantages accrue. However, the secondary channels proposed in the prior art do not translate well to laparoscopy where, as noted above, surgical conditions are much more severe. For example, the state-of-the-art expander in laparoscopy provides only for the gradual expansion of the surgical port, without any provision for a secondary or multiple lumens.

Furthermore, even in nonlaparoscopic settings the secondary channels of the prior art have not met with commercial success. A number of reasons may be postulated.

Although it is understood that a surgical access device must initially have a small cross-sectional profile for ease of insertion, the means for expanding that device have varied. Typically, such expansion means comprises a secondary or auxiliary channel having a lumen for the insertion of an endoscope or other endoscopic instrument. Thus, the main lumen of the surgical access device is formed by a hollow channel defined by a certain wall of thickness. The cross-sectional profile of the surgical access device is usually circular, although other profiles have been utilized. As used herein, "profile" will mean a cross-sectional profile unless otherwise specified. Thus, the goal of present access devices is to minimize their profile upon initial introduction. Following insertion, however, it is desirable to form a secondary channel in the device for the insertion of a second instrument in order to complete the intended procedure or another unanticipated procedure. This secondary channel is typically formed from a polymeric or rubberized elastic material. Due to their elastic nature, such secondary channels have substantial wall thicknesses. Moreover, in order to minimize the profile of the device upon insertion, these secondary channels must be collapsed in some fashion upon insertion. Thus, the cross-sectional wall thickness of the secondary channel must lie upon the outer diameter of the main channel, thus adding significantly to the overall profile of previous surgical access devices. This construction adds a new problem to the one the device is attempting to solve.

The most commonly proposed solution to the extra profile added by the secondary channel, is to surround it with an outer sheath or other elastic band, in order to hold it in a collapsed state around the outer diameter of the main channel of the surgical access device. However, this approach simply aggravates the problem due to the wall thickness of the outer sheath or banding. Moreover, these outer materials add to the radial resistance which must be overcome in order to push the instrument through the secondary channel. In addition, and quite significantly, the elastic nature of previous secondary channels presents severe frictional disadvantages, further intensifying the problem of instrument insertion. Moreover, in reusable systems, the outer sheathing or banding, which causes a secondary lumen to collapse, presents a substantial problem with respect to sterilization.

Another significant disadvantage of prior secondary channels is that they are elastically expandable, both longitudinally and radially. Thus, upon either insertion and/or deployment of secondary instrument, the channels may become loose or gathered. Thus, upon insertion of the instrument, there might be bunching or binding, which prevents the instrument from smoothly accessing its desired location. This requires the application of greater force on the instrument, thus increasing the pain and trauma to the patient which is intended to be avoided by the surgical access device. That is, most procedures of this type are performed on an out-patient basis with the patient undergoing only a local anesthetic. Thus, the difficulties associated with previous secondary channels, including their more frictional nature, increases the likelihood that the procedure will be uncomfortable and even traumatic for the patient.

Moreover, because of the elastic nature of previous secondary channels, they require an additional hollow tube to hold them in the open position for repetitive instrument insertion. Furthermore, there has been a lack of attention to leading edge design, so as to avoid contamination upon insertion of prior art surgical access devices. This is particularly a severe problem in connection with the reusable systems which require sterilization between use.

Moreover, the secondary channels of the prior art have not kept up with advancements in endoscopic design. Presently, smaller laparoscopes having an outer diameter of around 2 mm are available for laparoscopic procedures. However, surgical access devices available for use with such "microlaparoscopes," while perhaps minimizing the size of the port needed to gain access to the body, have not provided any means to reduce the number of ports for the procedure.

Thus, there is a severe need in the prior art for surgical access devices and methods of constructing and using the same which alleviate these problems associated with present laparoscopic procedures.

SUMMARY OF THE INVENTION

The present invention satisfies this need in the prior art by providing a laparoscopic introducer and a method for constructing and using same, wherein the profile of the introducer is minimized. Furthermore, the introducer is provided with one or more releasable guide channels for the post-introduction insertion of secondary instruments. Thus, the present invention reduces not only the size of the laparoscopic ports, but also the total number of such ports needed to perform a particular procedure. The introducer also allows a wide variety of procedures to be performed under only a local anesthetic and on an outpatient or office basis. Thus, the present method and apparatus drastically reduces the invasiveness and cost of laparoscopic procedures and allows many new ones to be performed more efficiently.

The present introducer and method is designed to be used with new smaller diameter and semi-rigid endoscopes or laparoscopes, but may also be used with larger diameter laparoscopes. Such scopes have an outer diameter of about 2 mm compared to the 10- to 12-mm scope and instrument ports currently used for laparoscopic surgeries. Thus, the use of these smaller diameter scopes is sometimes referred to as "microlaparoscopy." Such procedures, as noted above, can be performed in special procedure rooms, ambulatory surgery centers, or even in physicians' offices. The cost savings resulting from this shift to alternate sites is significant. Several recent studies indicate that microlaparoscopy without general anesthesia can be performed for $1,000–$1,250, compared to $5,000–$7,000 for hospital-based laparoscopic procedures. Furthermore, microlaparoscopy under IV anesthesia is well tolerated by the patient, and recovery times are reduced because these medications are much shorter acting than general anesthetics.

In accordance with the present method, access to the body is achieved by the use of a standard Veress needle of approximately 15 cm in length. Such needles are typically only about 2 mm in outer diameter, compared to typical trocar and sleeve combinations of approximately 5–10 mm in outer diameter. The Veress needle is slipped into the lumen of the present laparoscopic introducer, and the combination is advanced into the body. Because of the narrow profile of the introducer/Veress needle combination, less force is needed to penetrate the abdominal cavity. Thus, there is also a substantially reduced risk of injury to the vital organs below.

This narrow profile is maintained by the present introducer, despite the presence of an auxiliary or secondary guide channel formed on the exterior surface of the body of the introducer. Thus, upon introduction, the guide channel closely conforms to the outer surface of the introducer so that there is only a negligible increase in its overall profile. Furthermore, the guide channel remains set in this position upon introduction, without distortion or damage to the channel or increased pain or discomfort to the patient. To facilitate introduction, the guide channel material is naturally lubricous, both internally and externally. Thus, the guide channel of the present invention enjoys a number of advantageous characteristics, which are described below in more detail.

Once access to the body is achieved, the Veress needle is withdrawn, leaving the introducer in place to form the laparoscopic surgical port. A microlaparoscope is then placed through the tubing of the introducer in order to confirm correct entry into the peritoneal or abdominal cavity. Through a valve fitting formed on the introducer, insufflation gas (typically carbon dioxide) can be pumped into the abdomen in order to provide distention. Once distended, the inner cavity can be explored and visualized.

In order to perform the desired procedure, a secondary instrument is usually required. Thus, with the present introducer, a tapered dilator can be pushed through the guide channel in order to achieve the release and deployment of the channel. The dilator is useful in order to supply enough force to separate and dilate the tissues of the abdominal wall, including muscle and fascia. However, because this can be accomplished gently and gradually, increased pain and trauma to the patient is avoided, despite the increased profile of the port. Moreover, the guide channel may be provided with a flat wire reinforcement which protects the channel and facilitates insertion of the dilator. The nature of the guide channel material, as well as this guide wire reinforcement, avoids the binding or bunching of the dilator as it advances along the channel. Once the channel is dilated, the dilator rod is removed, and the guide channel is now ready for insertion of a secondary instrument.

A significant advantage of the present invention is that the laparoscope within the main channel of the introducer does not have to be removed before the dilation step. This speeds up the procedure and makes dilation much safer, since it can be directly observed by the physician. It also avoids multiple exchanges or insertions of instruments within the patient. Moreover, aligning the instrument to the targeted tissue is facilitated, since it travels along the same longitudinal axis as the laparoscope. This avoids the problems and distortions accompanying previous triangulation procedures.

The expandable laparoscopic introducer of the present invention, in one preferred embodiment, comprises a disposable sheath constructed from an inner tubing of stainless steel. This inner tubing compress the main or laparoscopic channel through which the laparoscope is inserted into the body. The proximal portions of the introducer comprises a housing with a laparoscopic port positioned therein. The housing is provided with an insufflation conduit and associated valve such that the conduit is in fluid communication with the main channel and thus the body. Surrounding the inner tubing is a split nylon tube which couples the present guide channel to the stainless steel tubing of the introducer. The guide channel is constructed from an extremely thin, but very strong and substantially noncompliant membrane. This guide channel membrane exhibits performance characteristics which make it preferred for this application.

The wall thickness of the guide channel membrane is so thin (approximately 0.001 inches in some embodiments) that it has only a negligible affect on the profile of the present surgical access device. This is true even though the membrane may be folded or doubled back on or around the outer wall surface of the surgical access device. Thus, the guide membrane of the present invention is compatible with very small diameter access devices which are more commonly being used with rigid and especially semi-rigid endoscopes. Accordingly, the surgical access device of the present invention is able to substantially reduce the pain and trauma associated with endoscopic procedures.

One important advantage of the present membrane is that it can be formed or set in position on the surgical access device. That is, by the use of moderate heat or other heat shrinking or heat forming techniques, the membrane can be "set" in order to closely conform to the outer surface configuration of the access device, thus maintaining a narrow or otherwise small profile. Moreover, outer elastic sheathing, straps, or binding of any type are unnecessary; thus, the profile of the access device is further minimized. An additional advantage of the present membrane is its lubricity. That is, the material in its natural state as formed on the access device is lubricous or otherwise less-adhesive, thereby facilitating inserting of the access device and reducing discomfort.

The guide channel membrane of the present invention can be constructed from any one of a number of highly oriented or cross-linked, noncompliant materials, including, without limitation, polymers. Such polymers may preferably undergo an extrusion process in order to achieve their high orientation status, resulting in their noncompliant and substantially inelastic nature. Moreover, such extruded polymers are also very strong and tough, and lubricous as pointed out above. In the preferred embodiment, one guide channel membrane material is polyethylene terephthalate ("PET"), although other materials within that group are possible, examples being polyolefins and their blends which can be highly orientated after radiation treatment and heat forming as found in the art of balloons for angioplasty catheters. Other materials include nylon and polyethylene which achieve orientation by pre-stretching whereby the material has high strength and little elongation when a load (stress) is exerted upon it.

The guide channel membrane may be formed from material having various thicknesses, depending upon the application of the particular surgical access device; however, thicknesses in the range of 0.0005–0.002 inches are preferred. Thus, it can be seen that such membranes do not add significantly to the profile of the access device.

Another advantage of the guide channel membrane of the present invention is that it is "releasable" upon dilation. That is, although heat formed or otherwise set so as to closely conform to the outer configuration of the access device, the membrane material can easily open up or release to form a secondary guide channel. In most cases, dilation can be achieved by the secondary endoscopic instrument itself, without a need for a dilator or obturator. Thus, these additional steps can be avoided. Moreover, the materials are also internally lubricous, thus, minimizing resistance to instrument insertion and advancement. The lubricous nature can also eliminate the need for additional layers of material, such as Teflon and their coatings, which can add profile as well as cost to the device. Since the membrane material is not elastic and is otherwise releasable, there is no radial resistance to instrument advancement. In addition, no internal support is necessary. That is, once the membrane material has been released, it forms a secondary channel which conforms to the nature of the tissue around it. In other words, if the tissue surrounding the access device and secondary channel is tight, the membrane will collapse and conform at the tissue in order to avoid unnecessary trauma. On the other hand, if the passage is expanded or dilated, the channel, following release, will maintain its general channel-like shape, without the need for any auxiliary internal tubing or support from any media such as fluid. Thus, the membrane will maintain its configuration even with the instrument removed.

The guide channel of the present invention is self-adjusting. That is, the membrane material will release to form a secondary channel which is only large enough to admit the passage of the instrument being advanced through it. Thus, the guide channel holds the instrument securely along its path as it is advanced to the distal end of the access device. This advantage also allows for insertion of instruments having various cross-sectional profiles, thus avoiding the need to design secondary channels specifically for certain instruments. In certain embodiments, perforations or slits may be formed in the guide channel in order to facilitate release or dilation.

As noted above, the guide channel membrane is noncompliant. Thus, it will not expand elastically upon insertion or dilation, either longitudinally or radially. It will be understood that the term "radially" is intended to mean in an outward direction, the cross-sectional configuration of the present guide channel not being limited to a circular or cylindrical configuration. Thus, the guide channel will not bunch up or bind as the instrument is advanced through it. Moreover, because of its toughness and strength, repetitive insertions of the instrument without failure are readily achievable, especially in tight or strong tissue, such as experienced in laparoscopic applications.

Upon withdrawal, the guide channel membrane is easily collapsible so as to minimize any pain or trauma. Moreover, with the application of a slight vacuum, the membrane will conform closely to the outer surface configuration of the surgical access device for easy withdrawal.

The surgical access device of the present invention can be constructed from inexpensive materials and in accordance with simple construction techniques. This is particularly true of the guide channel membrane. Thus, the access device is disposable, thereby avoiding problems associated with sterilization. Moreover, the membrane is compatible with any type of surgical access device, including introducers, endoscopic sheaths, catheters, cannulas, and endoscopes themselves.

In accordance with another advantage of the present invention, one embodiment of the membrane described above is used to form a guide channel on the surgical access device. Unlike secondary channels of the prior art, the present guide channel can be used to securely guide an instrument longitudinally along the introducer without lateral movement. Moreover, guide rails can be formed to further provide structure and rigidity to the secondary channel. The guide rails formed in the guide channel enable the instrument to arrive at a specific distal location with respect to the primary lumen, depending upon the procedure.

The guide platforms or rails can take on a number of configurations. Advantageously, however, due to the formable and thermoplastically settable nature of the channel membrane, the channel membrane can be folded or arranged with respect to the access device in a wide variety of ways.

The surgical access device of the present invention also exhibits a particular distal end design which avoids contamination. Upon insertion of the device, the instrument channel is sealed so as to avoid entry of tissue or foreign contaminating material. Due to the thermoplastic nature of the channel membrane, the seal can be accomplished by heat forming the channel at the distal tip. Alternatively, a narrow profile tip can be designed which plugs the distal opening of the secondary channel while still facilitating entry of the access device. Like the distal end of the present access device, the proximal end also features a particular "y" design which facilitates advancement of a secondary instrument into the guide channel while minimizing risk of damage to the device or discomfort to the patient. The proximal end of the access device is provided with a housing which gently introduces the instrument along a path which eventually becomes tangential to the main longitudinal axis of the access device. The housing which surrounds the proximal end is also provided with appropriate valves to control and regulate the in-flow and out-flow of distension media, irrigation fluid, or other fluid.

As noted above, the guide channel of the present invention can be integrally formed on the insertion tube of an endoscope or separately formed on an introducer, endoscopic sheath, and the like. In the latter case, the introducer can be designed and constructed so as to guide the entrance of the secondary instrument in a particular way in order to achieve a specific purpose, depending upon the procedure being accomplished. Moreover, the instrument can enjoy a lumen independent of any movement of the endoscope which is inserted through the main channel of the introducer.

In accordance with the method of construction of the surgical access device of the present invention, as noted above, the settable nature of the membrane material facilitates a number of construction arrangements and techniques. Thus, the membrane material can be pleated, folded or stored with respect to the access device on an exterior surface, interior surface, or other intermediate location. It can be coupled to the access device by a wide variety of means, including mechanical, adhesive, heat formation, etc.

Thus, in accordance with a preferred method, the surgical access device of the present invention is constructed from a main tube which provides a main channel for the access device. The main tube can be constructed from stainless steel tubing or a rigid plastic such as polycarbonate which can provide strength with little wall thickness. Typically, the main channel provides access for insertion or introduction of an endoscope; however, other instruments can be introduced into the patient as well through the main channel. The guide channel membrane is formed onto the main tube in the following manner. The membrane is provided in the form of a hollow tube, which is typically extruded to form that shape, so as to have an outer diameter which is greater than that of the main tube. The membranes can be constructed from PET tubing which can come in the form of balloon tubing which is pre-stretched and highly orientated for minimal elongation. Other constructions of membranes can use polyolefins and their blends, polyethylene, and nylons which are highly orientated or cross-linked. The guide channel membrane tube is placed over the main channel tube and positioned eccentrically with respect to the axis thereof.

A split tube sheath is mechanically clamped over the main tube capturing the guide channel membrane tube against the main tube. The split tube can be made from nylon 11 which has high strength with little wall thickness. Other materials such as polycarbonate, polyethylene, urethane, and the like can be employed. The split channel can be mechanically affixed to the main tube or be placed onto the main tube by a variety of adhesive agents or thermal bonding techniques. The actual width of the slit itself can vary which will affect the profile and guiding characteristics of the membrane channel. The excess membrane material, owing to the fact that its outer diameter is greater than that of the main tube, is allowed to escape through the slit in the sheath and extends outwardly therefrom. This excess material is then folded or otherwise stored with respect to the main tube in any one of a variety of ways so as to minimize the profile of the surgical access device. Typically, the excess membrane material is folded or doubled back on itself so as to closely conform to the outer surface configuration of the tube. An intermediate amount of heat, such as approximately 160° F., is then applied to the membrane material so as to heat form or set it in position closely conforming to the main tube.

In accordance with another method of construction and introducer embodiment, an even narrower profile introducer can be constructed without the need for an outer split sheath. In this case the guide channel membrane tube is heat bonded or otherwise coupled directly to the hypotube by adhesive or other means. To facilitate this construction, the membrane tube can be supplied in a multi-lumen or figure-8 configuration, wherein the membrane is constructed from an extrusion or other process. Moreover, one or more of the lumens may be collapsible, and the others may be noncollapsible, either due to their increased wall thickness or to rigidifying means such as hypotubes or reinforcement devices, etc.

In accordance with another step of the present method, a merge channel may be formed along the main channel in order to provide for the easy insertion of a secondary instrument into the guide channel. The merge channel can be constructed from a variety of materials including nylon 11 and other polymers as well as stainless steel which can be flexed yet retain radial integrity. As noted above, the merge channel is proximally located with respect to the surgical access device and remains substantially out of the body. In accordance with the present method, the merge channel tube is longitudinally aligned with respect to the axis of the main tube prior to the over-wrapping of the guide channel membrane tube. Thus, the proximal end of the membrane tube circumscribes both the main tube and the distal end of the merge channel tube and the guide channel is simultaneously formed around both the main tube and the merge channel tube to comprise the "y" junction of the surgical access device. To provide mechanical strength at this y junction, a housing or other mechanical clamping means is provided. The housing can take a variety of forms to provide ergonomic benefits to the operator or clinician. In construction, it can be made from a variety of injection molded plastics including polycarbonate, polysulfone, nylon, etc., or machined. It can be a part of the disposable introducer or a separate unit which is reusable, re-sterilized, and placed back onto the surgical access device by the operator prior to each use.

In another step of the present invention, the distal tip of the surgical device is sealed so as to prevent contamination or distortion of the guide channel upon insertion of the access device into the body. Likewise, at the proximal end of the access device, the main channel and merge channel are provided with the necessary valving for irrigation or distention media. The valving must prevent any leakage around an instrument or endoscope when these devices are placed through the ports and typically has an O-ring or washer type structure. In addition, they must contain structures such as duck-bill or star valves which prevent the backflow of media through the ports when no instrument or endoscope is through the port. These valves can be made from silicone, rubber, and other elastomeric materials which are known in the art.

Thus, in summary, the method of present invention for performing laparoscopy comprises the steps of providing an access device having a proximal end, a distal end, and an elongate body extending therebetween; said access device comprising a first lumen having a substantially fixed interior cross-sectional area and at least one second lumen defined at least in part by a substantially inelastic flexible wall, said second lumen having an internal cross-sectional area that is enlargeable from a first, reduced area to a second, enlarged area; advancing the access device into the patient while the second lumen is in the first, reduced cross-sectional area configuration; introducing an insufflation media through the first lumen to enlarge a working cavity in the patient; enlarging the profile of the second lumen from the first, reduced cross-sectional area to the second, enlarged cross-sectional area to provide percutaneous access to the cavity by way of said second lumen; and introducing an instrument into the cavity by way of the second lumen to perform a laparoscopic procedure. The present method further comprises the steps of forming an endoscopic port so as to provide access to a bodily cavity; providing a surgical access device for insertion through said port and into said bodily cavity, said access device having a first channel in an open position and a second channel in a substantially closed position; providing distention media through said first channel; inserting a laparoscope through said first channel in order to visualize said bodily cavity; dilating said second channel so as to provide auxiliary access to said bodily cavity; and inserting an instrument, endoscope, or other visualization device into said secondary channel and along substantially the same longitudinal axis of said first channel in order to perform said laparoscopic procedure.

Accordingly, the laparoscopic surgical access device of the present invention and the method of constructing and using it provide a substantial advance over the prior art.

BRIEF DESCRIPTION OF THE DRAWINGS

FIG. 2 is a side view of the present access device further illustrating, in combination with FIGS. 1, 1a, the method of the present invention for performing laparoscopic procedures, and more specifically the deployment of a secondary guide channel by means of a dilator which is shown advancing along the distal portion of the access device.

FIG. 3 is a cross-sectional view of the present access device taken along lines 3—3 of FIG. 2 illustrating the main or laparoscopic channel of the access device and a secondary guide channel which is shown in its initial storage or collapsed position with respect to the access device body and prior to the deployment of a secondary instrument through said guide channel.

FIG. 3a is a cross-sectional view of the present access device illustrating an alternative embodiment for folding or pleating the guide channel.

FIG. 3b is a cross-sectional view of the present access device illustrating an alternative embodiment for the guide channel which does not utilize a split sheath.

FIG. 3c is a cross-sectional view of the access device of FIG. 3b, illustrating the guide channel in its deployed or released position.

FIG. 4 is a cross-sectional view of the present access device taken along lines 4—4 of FIG. 2 illustrating the guide channel of the present invention in a released or distended state as a secondary laparoscopic instrument is advanced therethrough.

FIG. 9 is a cross-sectional view of yet another embodiment of the present laparoscopic access device illustrating a flattened guide rail or platform.

FIGS. 10 and 10a illustrate the distal portion of the present access device having a perforated or slit guide channel configuration.

FIG. 11 is a close-up side view of the distal tip of the present access device.

FIG. 12 is a longitudinal cross-sectional view taken through the proximal housing portion of the present access device in order to illustrate the merge channel for guiding a secondary instrument into the guide channel of the present invention.

DETAILED DESCRIPTION OF THE PREFERRED EMBODIMENTS

Figure 1:
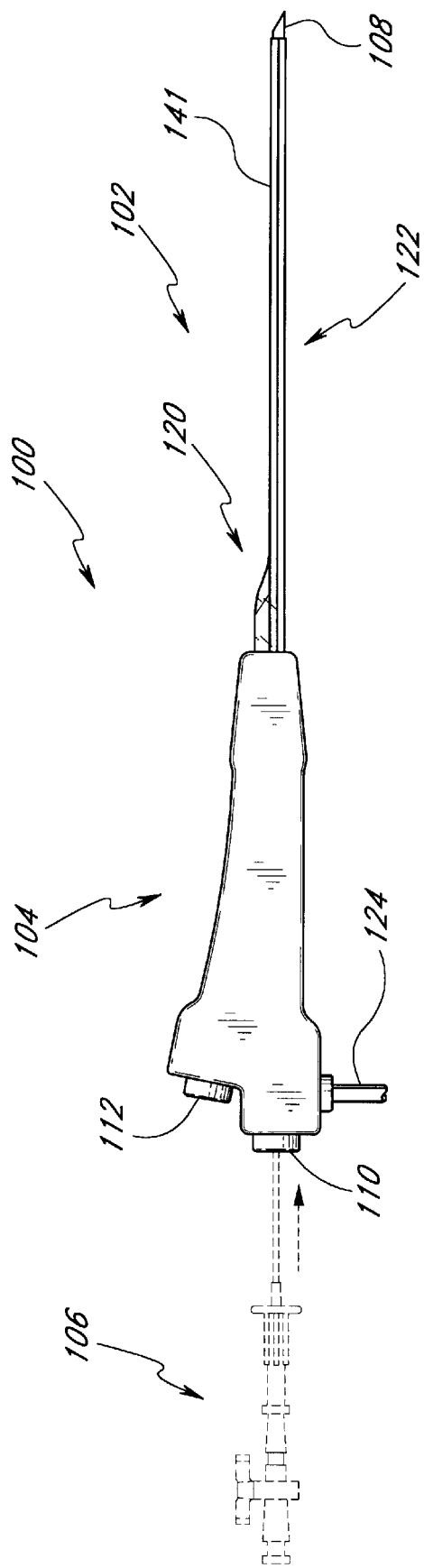
FIG. 1 is a side view of the laparoscopic surgical access device of the present invention illustrating in dotted lines a Veress needle used in combination with the access device to gain access into the patient's body.

With reference to FIG. 1, there is shown the laparoscopic surgical access device 100 of the present invention. In this case, a surgical introducer has been selected to illustrate the principles of the present invention; however, it will be understood that such principles apply equally well to all types of surgical access devices, as well as to other devices not necessarily limited to surgical access or laparoscopic procedures. In the broadest sense, the principles of the present invention encompass devices where secondary channels or other types of guide channels, expandable, distensible, or otherwise, are desirable or necessary in order to allow passage of some time of instrument. Thus, the fact that the present invention is described with respect to a laparoscopic introducer is illustrative only and not intended to be limiting in any respect.

Furthermore, it will be understood that the present invention is compatible with all types of instruments, including catheters, obturators, etc. Also, visualization devices used with the present access device are not to be limited to endoscopes, but also include all types of such devices, including fluoroscopes, etc. Thus, the terms "instrument" and "endoscope" are intended to be only illustrative and representative of the wide variety of devices that can be utilized in accordance with the present invention, and such terms are not intended to be limiting in any respect.

Laparoscopic Surgical Introducer

With further reference to FIG. 1, there is illustrated a laparoscopic surgical introducer 100 into which the principles of the present invention have been incorporated. In this case, the introducer is intended primarily for laparoscopic procedures, such as cholecystectomy, bipolar tubal sterilization, gamete intra-fallopian transfer ("GIFT"), directed biopsy, etc. However, a wide variety of laparoscopic procedures may be performed with the laparoscopic introducer of the present invention.

As shown in FIG. 1, the introducer 100 comprises a distal insertion portion 102, which is inserted into the patient's body, and a proximal housing portion 104, which generally remains outside of the patient's body. As noted above, access into the patient's body is achieved through a stab incision in order to form a laparoscopic port. Thus, the present introducer 100, in combination with a Veress needle 106 shown in dotted lines, is advanced into the body through the incision, which can be aided by a sharp bevelled tip 108 formed at the distal end of the introducer 100; however, blunt distal tips or conically beveled tips may also be utilized. The Veress needle 106 is shown partially inserted into a main or laparoscopic port 110 of the proximal housing of the introducer. Situated adjacent the laparoscopic port 110 is a secondary port 112 for receiving a dilator 114 or other secondary surgical instrument as explained below in more detail in connection with FIGS. 1a and 2. The details of construction of the insertion portion 102 of the introducer are described below in more detail in connection with FIGS. 3 and/or 4, while the details of the housing portion 104, including an insufflation conduit 116, are described and illustrated below in connection with FIGS. 12 and 13.

It will be noted that the terminology of main or laparoscopic port 110 and secondary or instrument port 112 is merely illustrative since a laparoscope 118 is typically inserted into the main port 110 of the introducer, while a dilator or other secondary instrument 114 is inserted through the auxiliary or secondary port 112. However, in accordance with the principles of the present invention, this arrangement can be reversed, or any other of a wide variety of instruments may be used in connection with the various ports of the introducer. In addition, two or more auxiliary ports may be formed on the introducer, depending upon the nature of the procedure to be performed.

Although not readily apparent from FIG. 1, the insertion portion 102 of the introducer 100 is provided with a guide channel 120 which is illustrated and described in more detail in connection with FIGS. 3–4. The guide channel 120 of the present invention is mounted on or is otherwise incorporated into the main laparoscopic channel 110 which forms the basic cross-sectional profile of the insertion portion 102 of the introducer 100. In the position shown in FIG. 1, which is before or during insertion of the introducer 100, the guide channel 120 tightly hugs the body of a laparoscopic channel 122. Moreover, the guide channel 120 in this position is virtually unnoticeable to the eye or touch. Thus, the guide channel 120 adds only a negligible dimension to the profile of the introducer 100, thereby minimizing pain and discomfort to the patient.

It will be further noted from FIG. 1 that the guide channel 120 closely conforms to the outer configuration of the insertion portion 102 without the need for outer sheaths or bands which would increase the profile thereof. Moreover, since the guide channel 120 is formed, in one preferred embodiment, on the exterior wall of the laparoscopic channel 122, its natural lubricity provides an important advantage with the ease of insertion of the introducer. However, it will be noted in accordance with the present invention that the guide channel 120 may also be formed on or within the laparoscopic channel 122 or in other configurations with respect to the introducer. Moreover, as noted above, multiple guide channels may be provided.

Accordingly, the laparoscopic introducer 100 of the present invention provides a substantial advantage in reducing the invasiveness and cost of laparoscopic procedures. Because of its narrow profile and ease of insertion, it can be very effectively used in combination with small diameter rigid and semi-rigid laparoscopes, as well as larger diameter endoscopes. The distal end of the introducer may be beveled, blunt, or conically tapered to facilitate insertion. Moreover, such procedures can be performed with less trauma to the patient, allowing them to be performed on an out-patient basis or in a physician's office. Moreover, new categories of laparoscopic procedures are now available.

These and other advantages of the present introducer and its method of use are described below.

Method of Use

Figure 1A:
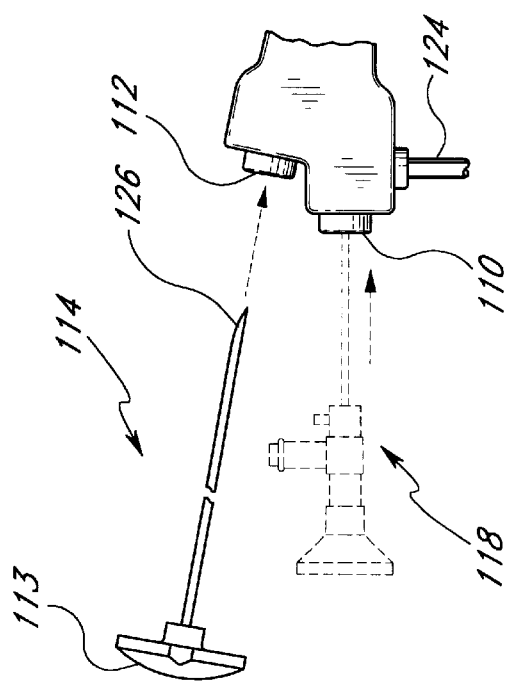
FIG. 1a is a partially broken-away close-up side view of the access device of FIG. 1 illustrating in dotted lines a laparoscope inserted in the main or laparoscopic channel of the access device and a dilator about to be inserted into the secondary instrument port of the access device.

A method of performing a laparoscopic procedure may be described in connection with FIGS. 1, 1a and 2. However, it will be understood that laparoscopic procedures may vary slightly from one procedure to the next, depending upon the specific purpose of the procedure. Thus, the following description is intended to be generally illustrative only and not limiting as to the present laparoscopic method.

As noted above, the present introducer 100 forms a laparoscopic port when it is introduced into the patient's body with the Veress needle in place. Subsequently, as illustrated in FIG. 1a, the Veress needle 106 is removed and a laparoscope 118 is inserted through the main laparoscopic port 110 and down along the main channel 122 of the insertion portion 102 of the introducer into the patient's body. This placement of the laparoscope 118 allows the surgeon to confirm correct entry into the peritoneal cavity. Via a conduit 124 illustrated in FIG. 1, insufflation gases are then pumped into the cavity through the laparoscopic channel 122 in order to distend the abdomen. Once distended, the inner cavity can be explored and visualized more fully.

In order to perform the desired diagnostic or surgical procedure, it then becomes desirable to insert a secondary instrument into the cavity under the visualization advantages provided by the laparoscope 118. In order to achieve such insertion, the guide channel 120 on the introducer must first be dilated or otherwise deployed by means of a sturdy dilator 114 shown adjacent the instrument port 112 in FIG. 1a. Although a number of dilators are adequate, in a preferred embodiment of the present invention, the dilator 114 is provided with a distal tip 126 which is bevelled along only one side, as shown in FIG. 1a. The advantages of this dilator configuration are illustrated in connection with FIG. 2.

FIG. 2 illustrates the present introducer with the dilator 114 extending through the instrument port 112 and the proximal housing 104, and advancing through the guide channel 120 formed on the laparoscopic channel. Thus, it will be noted that the nontapered side of the dilator 114 rides against the laparoscopic channel 122 while the tapered side is used to dilate or deploy the guide channel 120. This dilator 114 must be sufficiently rigid in order to supply enough force to separate and dilate the tissues of the abdominal wall, including muscle, fascia and peritoneum. Once the dilator 114 has advanced to the region of the distal tip 108 of the introducer, it can be withdrawn leaving the guide channel 120 in a deployed position. However, because of the unique characteristics of the membrane from which the guide channel 120 is constructed (which is described in more detail in connection with FIGS. 5 and 6), the guide channel 120, due to the newly dilated tissue surrounding the introducer, will substantially retain its dilated position. In other words, the introducer can be said to be self-supporting, retaining its patentency without the need for an inner tube or other supporting means. Furthermore, the surrounding tissue will more easily be redilated. Thus, the insertion of a secondary surgical instrument through the guide channel 120 and into the bodily cavity is facilitated.

Therefore, in accordance with an important advantage of the present invention, this secondary instrument can be inserted, advanced, and utilized in full and immediate vision provided by the laparoscope 118, which line of vision is along the same longitudinal axis of the scope. Thus, the visual distortions associated with triangulation are avoided, not to mention a reduction of total number of surgical ports. Moreover, the laparoscope 118 does not have to be removed in order to insert this instrument, and multiple exchanges or insertions of instruments within the patient are avoided.

These and other attendant advantages are achievable, in large part, due to the guide channel 120 of the present invention. The guide channel which does not significantly increase the cross-sectional profile of the introducer 100 upon insertion, but it can be dilated and retained in that position due to the gradual dilation of the laparoscopic port, as achieved by the dilator 114 described above, as well as the concurrent dilation of the tissues surrounding the entry port. Thus, as noted below, the guide channel 120 will readily conform to the force conditions surrounding it (whether they be imposed by instrument or anatomy), but will retain its configuration unless those conditions change. These and other characteristics of the present guide channel 120 are described below.

Guide Channel

The guide channel 120 of the present invention can be described in more detail in connection with the cross-sectional illustrations of FIGS. 3–4.

FIG. 3 is a cross-sectional view of the insertion portion 102 of the present introducer 100 prior to the release or deployment of the guide channel 120 by the dilator 114. Thus, with reference to FIG. 2, the cross-section of FIG. 3 is taken at lines 3—3 which are ahead of the advancing dilator 114. FIG. 3 illustrates a main or laparoscope lumen 130 for the insertion of the laparoscope 118 or other instrument (although, the laparoscope 118 is not shown in FIG. 3 for clarity of illustration). This lumen 130 is formed by the laparoscopic channel 122 which may comprise a tube 132 of various constructions. The laparoscopic tube 132 is in turn surrounded by a larger diameter split tube or sheath 134. The split in the sheath 134 defines a slit or longitudinal opening 136. Sandwiched between the inner laparoscopic tube 132 and the outer split sheath 134 is a membrane 140 which forms the present guide channel 120. This membrane 140 can initially be formed in the shape of a tube or other construction.

As shown in FIG. 3, the membrane 140 surrounds the inner laparoscopic tube 132 but, due to its greater diameter, also extends out of the longitudinal opening 136 in the split sheath 134. This excess membrane material may be folded back onto an outer surface 135 of the split sheath 134 to form a double-layer of the membrane 140 along a partial circumference of the introducer 100. Likewise, the folding pattern of the pleats may be such that all of the pleat is on one lateral side of the introducer or the other, rather than the two equal pleats shown in FIG. 3a.

This pleated or folded-back portion 141 shown in FIG. 3, forming pleats 137, 139, is that portion which defines the guide channel 120 for the instrument 114, as illustrated in more detail in FIGS. 2 and 4. However, as illustrated in FIG. 3, prior to instrument deployment, the guide channel 120 is defined by a membrane 141 which closely conforms to the outer surface 135 of the split sheath 134. For example, the lateral edges of the pleats 137, 139 can be provided with thin creases or seams 131, 133, which can be formed and set in the membrane material. Thus, the narrow profile of the introducer 100 is maintained. In addition, because of the close conformity of the guide channel membrane 140, it is less likely to be distorted or disturbed upon insertion of the introducer 100 into the body. Thus, the guide channel 120 maintains its structural integrity and avoids patient discomfort even before insertion of the secondary instrument 114.

Due to the forces necessary to dilate the guide channel 120, one preferred embodiment of the present introducer comprises a guide channel 120 with a reinforcing device 128 positioned therein. As shown in FIG. 3, this reinforcing device 128 can preferably take the form of a flat wire or other force distribution mechanism so that the dilation forces do not cause damage to the guide channel membrane 140. This reinforcement device 128 can also facilitate insertion of the dilator 114 and other secondary instruments by providing a smooth riding surface. Moreover, the reinforcement device 128, in combination with other guide channel designs, can provide enhanced guiding and tracking characteristics, as described in more detail below in connection with FIGS. 7–9.

Preferably, the present reinforcement device 128 takes the form of a flat wire having a thickness of between about 0.001–0.004 inches, and having a width of between about 0.040–0.300 inches. The flat wire is preferably constructed from stainless steel or other sturdy material. The flat wire is positioned longitudinally along the laparoscopic channel 122, but within the folds of the guide channel 120. Thus, the dilator or secondary instrument will ride along the reinforcement device 128, as shown in FIG. 4.

The membrane 140 which comprises the guide channel 120 can be extremely thin, ranging in thickness between 0.0005" and 0.002", preferably being about 0.001". Thus, even when doubled back on itself and lying on the outer surface 135 of the split sheath 134, the guide channel 120 adds only a negligible thickness to the profile of the surgical access device 100. Moreover, the guide channel in its pre-release position 141 shown in FIG. 3 will hold a set in this position and does not require any external elastic sheets or strapping to bind it in position on the introducer 100.

It will be understood, as noted above, that the present guide channel 120 can be formed on or in connection with surgical access devices of a wide variety. Moreover, in its pre-release position 141 (which it assumes prior to and even during insertion of the access device 100 into the body, but prior to deployment of an instrument through the guide channel 120), the guide channel 120 can be stored, wrapped, or folded in a number of configurations, other than that shown in FIG. 3.

For example, FIG. 3a shows multiple pleats or folds 237, 239 of pleated portion 241 in the membrane 140 which will facilitate a larger membrane channel 120 and can follow a multitude of folding patterns which preferentially unfold upon the exerted force of the insertion element. The additional material which constitutes these multiple folds 241 will allow for larger instruments to pass through the membrane channel 120.

Figure 7:
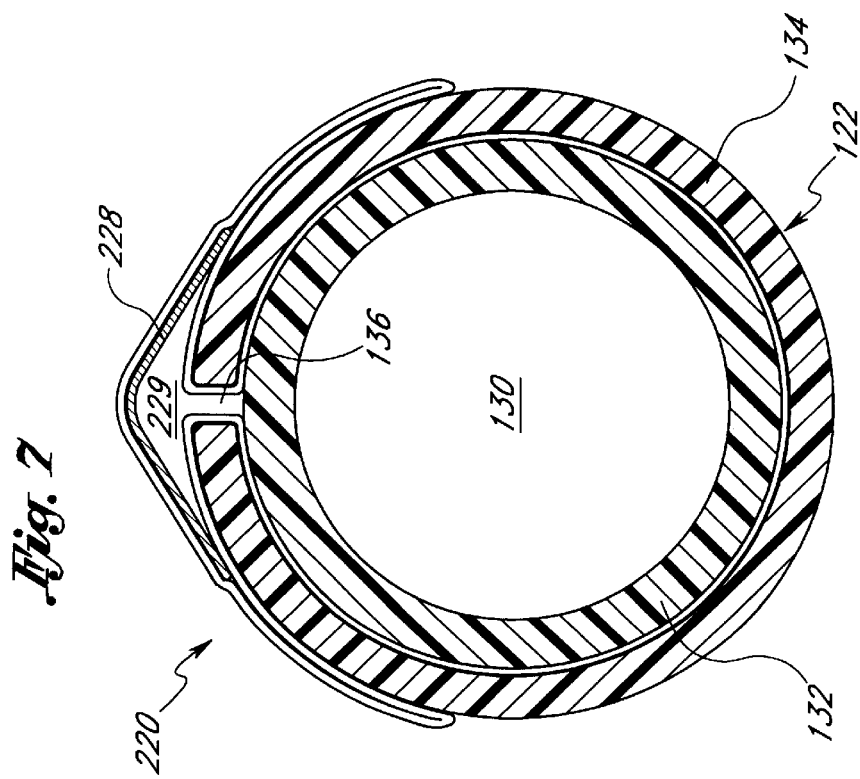
FIG. 7 is a cross-sectional view of the laparoscopic access device of the present invention illustrating an alternate embodiment of the guide channel.

Although the method of construction of the introducer 100 of FIG. 2 is shown and described in more detail in connection with FIG. 14, it will be understood that the laparoscopic tube 132 can be constructed from a wide variety of materials which provides rigidity and protection for the laparoscope 118. Preferably, such a tube 132 can take the form of a stainless steel hypotube. Thus, the tube 132 can provide the rigidity necessary for initial insertion (especially in difficult procedures such as a laparoscopy), and can be used to move tissue without fear of damage to the laparoscope 118 within. Moreover, the tube 132 can take on a bend or curve, as illustrated in FIG. 7, to facilitate a particular procedure. With advancements in rigid and semi-rigid laparoscopes, such curves or bends in introducers can facilitate intricate navigational procedures while not damaging the laparoscope. The curves and bends also direct the visualization area of the laparoscope to preferentially view anatomical structures not on the axis of the insertion point in the body.

The outer split sheath 134, in its typical construction, is smooth and lubricous in order to facilitate insertion of the introducer 100. It may be constructed from a durable, bio-compatible polymeric material, such as nylon, polyethylene, urethane, etc. Preferably, nylon 11 can be utilized.

It will be noted in connection with FIG. 3 that typical introducer construction will include both the laparoscopic tube 132 and the outer nylon layer 134. Thus, the guide channel 120 of the present invention does not significantly increase the profile of such an access device 100. In this connection, a number of cross-sectional introducer configurations will be readily apparent to those of ordinary skill in the art, including noncircular configurations. In addition, a wide variety of laparoscopic tube and split sheath wall thicknesses are within the realm of the person of ordinary skill; however, preferably, the laparoscopic tube 132 would have a wall thickness of approximately 0.008" while the split sheath 134 would have a wall thickness of approximately 0.005".

On the other hand, the versatility of the guide channel of the present invention allows it to be incorporated into introducers of even narrower profiles. For example, FIG. 3b illustrates a cross-sectional view of an alternate embodiment of the present introducer which does not utilize an outer split sheath to capture a guide channel membrane 340 onto a stainless steel hypotube 332. In this case the guide channel membrane 340 can be heat bonded or otherwise coupled to the tube 332 by adhesive or other means. To facilitate this construction, the guide channel membrane 340 can be supplied in a multi-lumen or figure-8 configuration, as illustrated in FIG. 3c, with one lumen 330 of the membrane 340 being mounted on the hypotube 332, leaving the second lumen 342 to be folded or pleated thereabout to provide a guide channel 324 in the stored position having pleats 337, 339. Thus, FIG. 3c illustrates this mounting position prior to the folding of the membrane 340, which position is shown in FIG. 3b. It will also be noted in connection with the embodiment of FIGS. 3b and 3c that guide channel membranes having multiple lumens can be provided and mounted on the hypotube in this or another manner, and then folded and set in position about the tube in order to provide an introducer with extremely narrow profile. Thus, three, four, or more membrane tubes can be mounted, either jointly or separately, on the introducer so as to provide multiple lumens. In addition, one or more of the tubes (which can be constructed from an extrusion or other process) may be collapsible, while others may be noncollapsible, due either to the wall thickness of the membrane extrusion or some other rigidifying or reinforcing mechanism (such as a hypotube or the like).

With reference to FIG. 4, there is shown cross-sectional view of the present introducer 100 through the insertion portion 102 where the instrument 114 has already advanced. In this case, the instrument 114 almost completely occupies a lumen 142 defined by the guide channel 120 of the present invention. As shown in FIG. 4, the guide channel 120 is shown releasing its predeployment position to allow the instrument 114 to easily pass along the guide channel 120 and into the patient.

The guide channel 120 of the present invention may be constructed from a membrane 140 which exhibits a number of advantageous characteristics. For example, in addition to its external lubricity, the membrane 140 is also internally lubricous to facilitate the deployment of the instrument 114. The physical characteristics of the membrane 140 also allow the guide channel 120 to be self-adjusting. That is, as shown in FIG. 4, the guide channel 120 releases only to the extent necessary to accommodate the particular instrument being inserted through it. If not needed, the membrane 140 remains folded in its set position in the region indicated by arrows 144 of FIG. 4. These advantageous characteristics allow the guide channel 120 to accommodate a number of instruments of various cross-sectional dimensions without significantly increasing the profile of the introducer 100.

Likewise, if the instrument 114 is removed from the guide channel 120, the membrane 140 causes it to maintain approximately the same position as it did with the instrument 114 inserted within, thus facilitating reinsertion of the same instrument or another instrument. For instance, in this case of removing multiple portions of tissue from the body, it may be necessary to remove tissue and then reinsert the instrument 114 back through the guide channel 120 to remove more tissue. Thus, there is no radial resistance to reinsertion which reduces the risk of damage to the guide channel 120 and discomfort to the patient. If the instrument 114 is withdrawn upon completion of the procedure, the guide channel 120 is readily collapsible upon withdrawal of the introducer 100 so that pain or trauma to the patient is avoided. Also, if desired, the guide channel 120 can be evacuated of fluids in order to facilitate its collapse prior to withdrawal.

As noted above, the guide channel membrane 140 is noncompliant both longitudinally and radially. Thus, it does not exhibit elastic characteristics which might cause the guide channel 120 to bunch up or bind as the instrument 114 is advanced therethrough. Moreover, the guide channel membrane 140 is malleable, meaning that it tends to conform to the pressures and forces exerted upon it by ambient conditions, including anatomy, tissue, and other media. This feature advantageously tends to reduce resistance to movement of the access device 100 and enhance patient comfort. On the other hand, in the absence of such ambient forces, the membrane 140 maintains its position and configuration, having somewhat of a "memory" in this regard.

A number of materials can achieve these advantages of the guide channel membrane 140 of the present invention. For example, inelastic polymers or other pleated, woven, or braided materials can be utilized. Preferably, however, highly orientated or cross-linked, noncompliant polymers can be utilized as a guide channel membrane material. Such materials tend to be thermoplastically settable, with glass transition temperatures greater than room temperature. In addition, such polymers are semicrystalline and deformable in the crystalline state. One preferred example of such a polymer is polyethylene terephthalate ("PET"), although other polymers are possible. For example, polybutyl terephthalate may be utilized as a guide channel 120, as well as nylon 6 or nylon 66. These materials, as well as others, exhibit the advantages described above.

Figure 5:
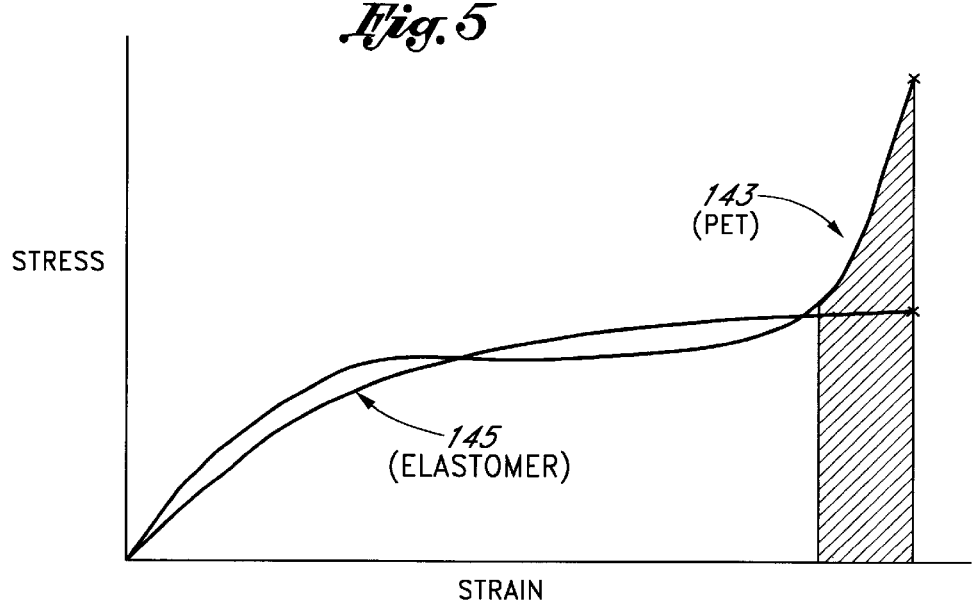
FIG. 5 is a graph illustrating the stress-strain relationship of oriented PET, as used for the guide channel membrane of the present invention, in comparison with typical elastomer.

In the case of PET, FIG. 5 illustrates the noncompliant (stress/strain relationship) of oriented PET as compared with a typical elastomer. A PET curve 143 in the graph shows a shaded region which depicts the behavior of a highly-orientated PET which has been pre-stretched. These stress-strain properties relate to a material which has high strength and very little elongation when a load is exerted upon it. Conversely, an elastomer behaves different in this and all sections of its curve 145 on the graph by elongating with little additional stress.

Figure 6:
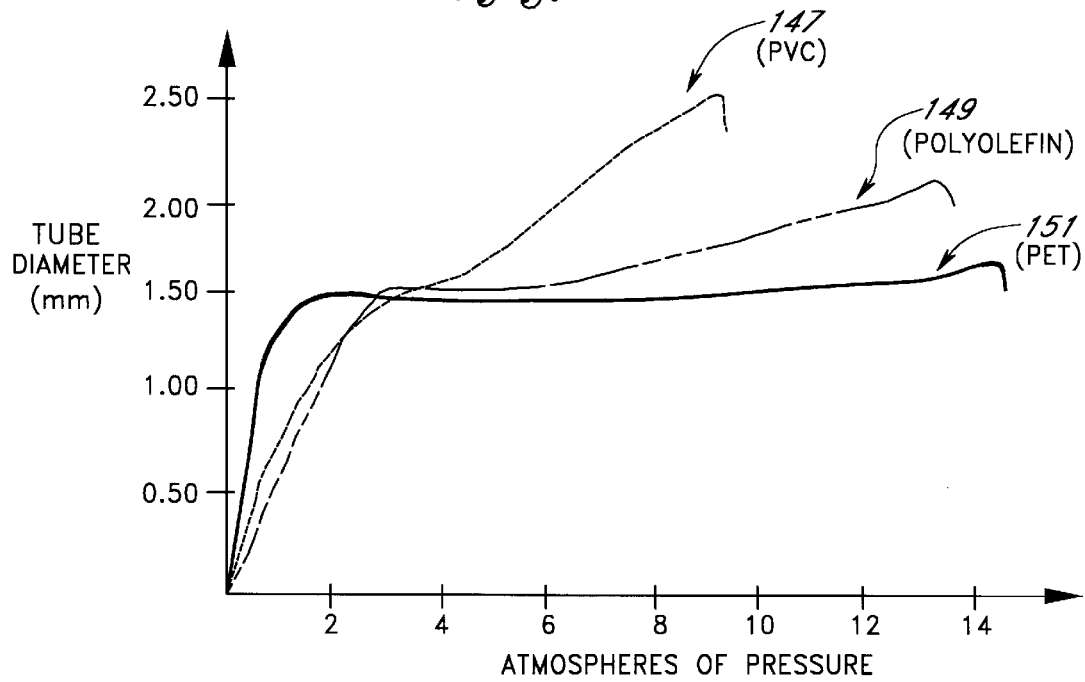
FIG. 6 is a graph illustrating the relationships between tube diameter and internal pressure for tubes constructed from PVC, polyolefin and PET material.

In addition, FIG. 6 illustrates the relationships between tube diameters and internal pressure for tubes comprising PVC 147, polyolefin 149 and PET material 151. In the graphs in FIG. 6, plots are shown for a closed vessel structure such as a balloon for various materials in which the outer diameter measurement is plotted versus the internal pressure applied. In this example, the PET material 151 demonstrates very little distension with greater internal pressure as a result of its high strength and low elongation in comparison to the polyolefin and PVC materials 149, 147 used for this example.

Alternate Guide Channel Designs

Figure 8:
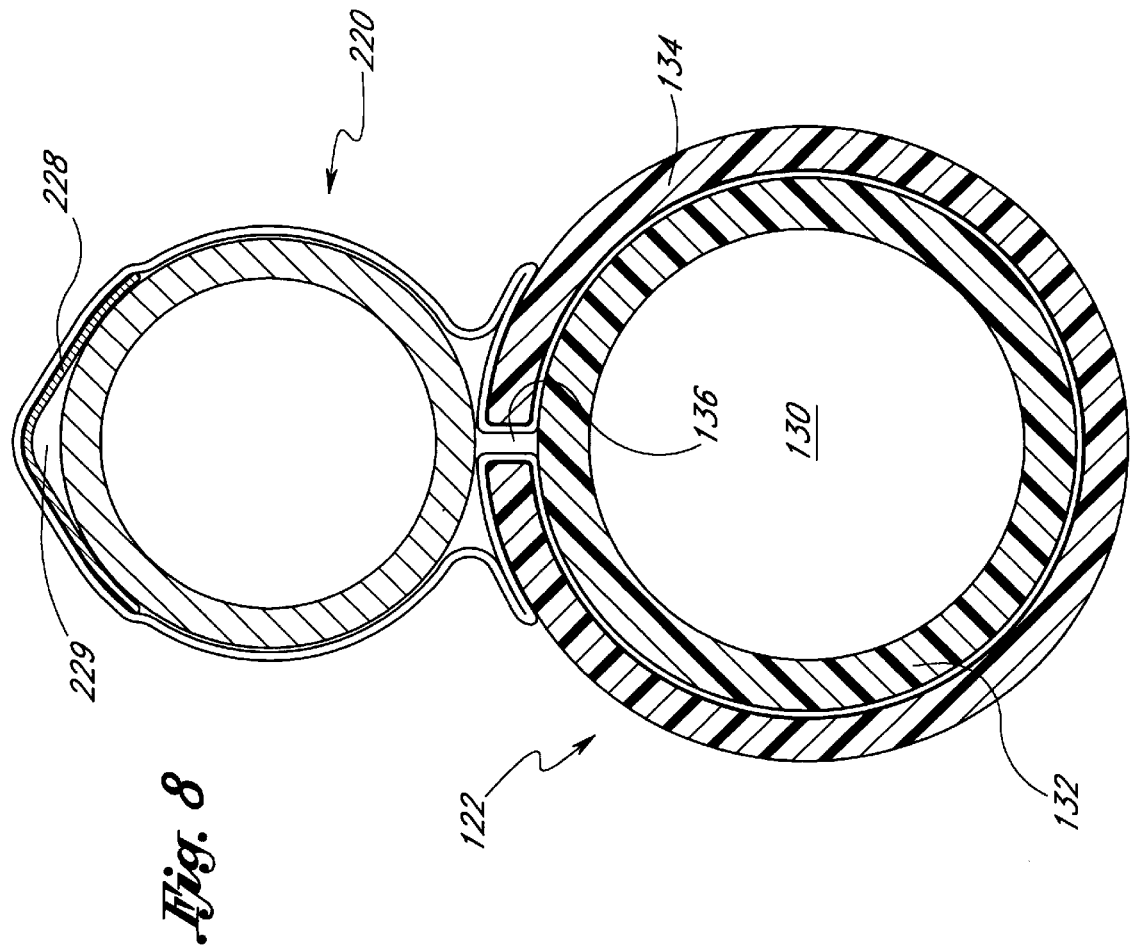
FIG. 8 is a cross-sectional view of the access device of FIG. 7 illustrating the insertion of a secondary instrument along the guide channel.

FIGS. 7–9 illustrate other features of the guide channel including its ability to securely guide the dilator 114 or instrument into a specific location with the patient's body. Referring to FIG. 7, there is shown a cross-section of a nondilated guide channel 220 including a concave reinforcement device 228. In this case, the internal flat wire which forms the reinforcement device 228 is provided with a concave depression or recess 229 which produces additional guidance for the dilator and/or secondary instrument. This recess 229 serves to keep the instrument from "walking" off the laparoscopic channel 122 or otherwise deviating from its longitudinal path along the insertion portion 102 of the introducer.

As shown in FIG. 8, the recess 229 formed in the flat wire 228 can, in combination with the slit 136 in the split sheath 134, form a track for the secure guidance of the dilator or instrument. Thus, in this embodiment the instrument 114 is not likely to move laterally along its path, which movement would cause pain and discomfort to the patient and possible damage to the guide channel 120. Certainly, a wide variety of guide channel tracking designs are within the scope of the present invention. Thus, for example, illustrated in FIG. 9 is yet another cross-sectional view of an alternate embodiment of the present introducer in which a split sheath 334 is flattened in order to provide a guide platform 148. Moreover, guide rails 150, 152, in addition to the slit 336, can be provided to provide even greater instrument guidance. These guide rails may be provided with upward projections (not shown) in order to provide even more secure guidance to the sides of the instrument.

The guide channel 120 of the present invention accommodates a rigid or semi-rigid instrument which may be inserted through the guide channel. As noted above, the guide channel membrane 140 is constructed from an extremely strong material in order to withstand the stresses on it caused by a instrument advancing therethrough. Nonetheless, it is important that the secondary instrument being advanced through the guide channel 120 be provided with a smooth and straight passage. Any slippage or lateral movement may cause damage to the guide channel 120 and/or discomfort to the patient.

Moreover, the guide channel 120 may be located at a number of different circumferential locations with respect to the main or endoscopic channel 122, and the main channel 122 may be curved. Thus, the guide channel 120 may be located at the bottom of the main channel curvature, which could be considered "inboard" with respect to the curvature of the introducer. However, the guide channel 120 may also be positioned, as needed or desirable for a particular procedure, "outboard" of the introducer (e.g., on the upper portion of the introducer), or "sideboard" (e.g., on one or more lateral sides of the introducer).

Therefore, in accordance with an important advantage of the present invention, the surgical access device can be used to guide an instrument along a specified path with respect to the main channel 122 so that it achieves accurate placement with respect to a specific location at the distal end of the access device 100.

Distal Portion

FIGS. 10 and 10a illustrate an alternate embodiment of a guide channel 218 of the present invention, which is characterized by a perforated or serrated guide channel membrane 240. As noted in FIGS. 10 and 10a, the guide channel membrane 240 is provided with a reduced diameter in the region of its distal tip 154. However, in this region or at other regions along the longitudinal length of the guide channel 218, the membrane 240 is perforated or serrated in order to facilitate its release as a secondary instrument 212 is advanced. Furthermore, the perforations or slits can be such that the guide channel 218 opens up completely in order to allow instrument access to the lateral regions of the access device. Such perforated or serrated guide channels 218 also provide other guide channel storage options, as well as other advantages which will be apparent to one of ordinary skill.

FIG. 11 illustrates one embodiment of a distal tip 108 of the present introducer 100. In this embodiment, the tip is beveled so as to facilitate the insertion process; however, the extreme distal tip may also be rounded or blunt in order to avoid damage to internal tissue. The guide channel at the distal tip 108, which is shown folded back on the outer surface 135 of the split sheath 134, can be securely sealed to the body of the introducer by a heat seal process. Thus, the guide channel 120 is sealed and is impervious against contamination or distortion as the access device 100 is introduced into the body. In an alternative embodiment of the distal tip, the distal end of the introducer may be shaped so as to have an annular mound at the distal tip of the guide channel and just proximal of the distal tip of the access device. Likewise, this mound can serve to protect the distal end of the guide channel against contamination or damage as the access device is introduced into the body and navigated through its various anatomy.

Proximal Housing Portion

As explained above in connection with FIG. 1, the proximal housing portion 104 of the present invention surrounds the main laparoscopic channel 122 and a merge channel 162 positioned above it in FIG. 12. The merge channel 162 allows an endoscope 110 or secondary instrument 114 to be inserted through it for deployment through the guide channel 120, shown in its predeployment position in FIG. 12. The merge channel 162 also allows a proximal handle 113 of the instrument 114 to be offset or displaced with respect to any laparoscope or instrument inserted in the main channel 122 in order to facilitate use of the access device 100 by the surgeon.

Figure 13:
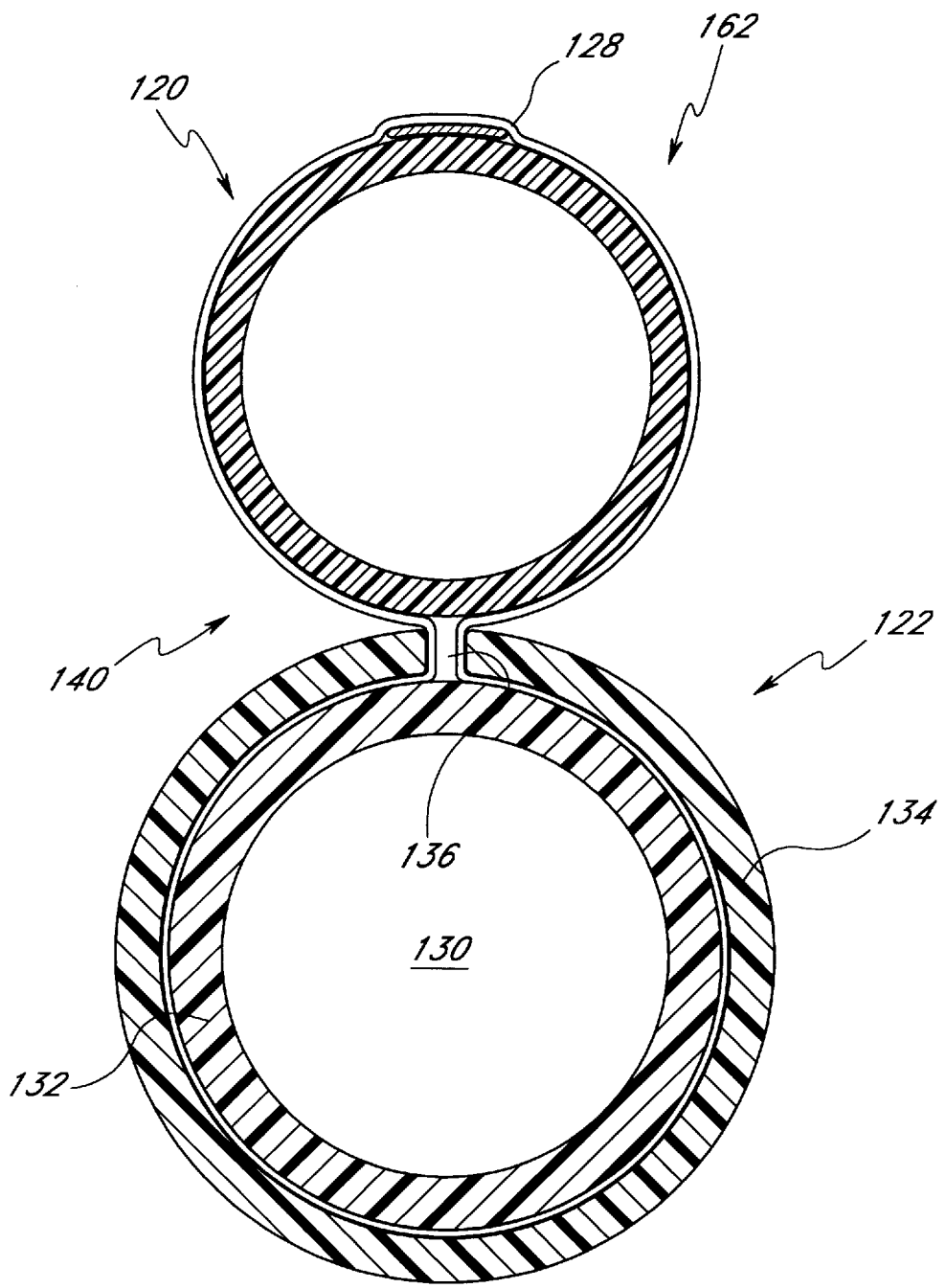
FIG. 13 is a cross-sectional view of the proximal housing portion of the present access device taken along lines 13—13 of FIG. 12 and illustrating the merge channel positioned adjacent to the main or laparoscopic channel.

With reference to FIGS. 12 and 13, the proximal housing portion 104 of the surgical access device 100 of the present invention can be described. FIG. 12 is a partial cross-sectional view of the side of the access device 100, while FIG. 12 is a cross-sectional view taken along lines 13—13 of FIG. 12 in which is illustrated the piggyback arrangement of the main or laparoscopic channel 122 and the merge channel 162 of the housing 104.

With reference to FIG. 12, it will be seen that the merge channel 162 converges upon the main channel 122 at a shallow angle φ, gradually becoming asymptotic or tangential thereto. The merge angle φ should be sufficient to allow a slight bending or curvature in the instrument being inserted through the merge channel 162 and into the guide channel 120; preferably, an angle φ of about 4°–30° is satisfactory with 11° preferable.

At the extreme proximal end of the housing portion 104, there is shown an inflow conduit 124 associated with the main channel 122. Depending upon the procedure being performed, the inflow conduit 124 may also be utilized to pass distention or irrigation media down the main channel 122 to the distal end of the access device 100. Having the distension media run through the main tube 132 and around the laparoscope 118 also allows for fluid to travel across the optics at the distal end of the laparoscope 118 keeping this area free of blood and debris thereby improving visualization. An outflow conduit (not shown) can be provided to provide aspiration or other evacuation of smoke during laser or electrical surgery. Duckbill valves 166, 168 are formed at the main or laparoscopic port 110 and at the instrument port 112 in order to prevent the escape of fluids prior to insertion of the instruments into these respective channels. Likewise, O-ring structures or washer elements prevent the escape of fluids around an endoscope or instrument when inserted through the ports 110, 112. However, it will be understood that other types of valving and conduit mechanisms can be utilized in connection with the present access device.

The cross-sectional view of FIG. 13 also illustrates the association of the guide channel membrane 140 with respect to the merge channel 162. That is, the membrane 140 is shown extending through the slit or neck 136 in the split sheath 134 and completely around the merge channel 162. Advantageously, the guide channel membrane material can be heat formed onto both channels in order to provide some rigidity and strength to the proximal housing portion 104 of the access device 100. In fact, the membrane 140 can be extended proximally any desired distance, as shown in FIG. 12.

Method of Construction

Figure 14:
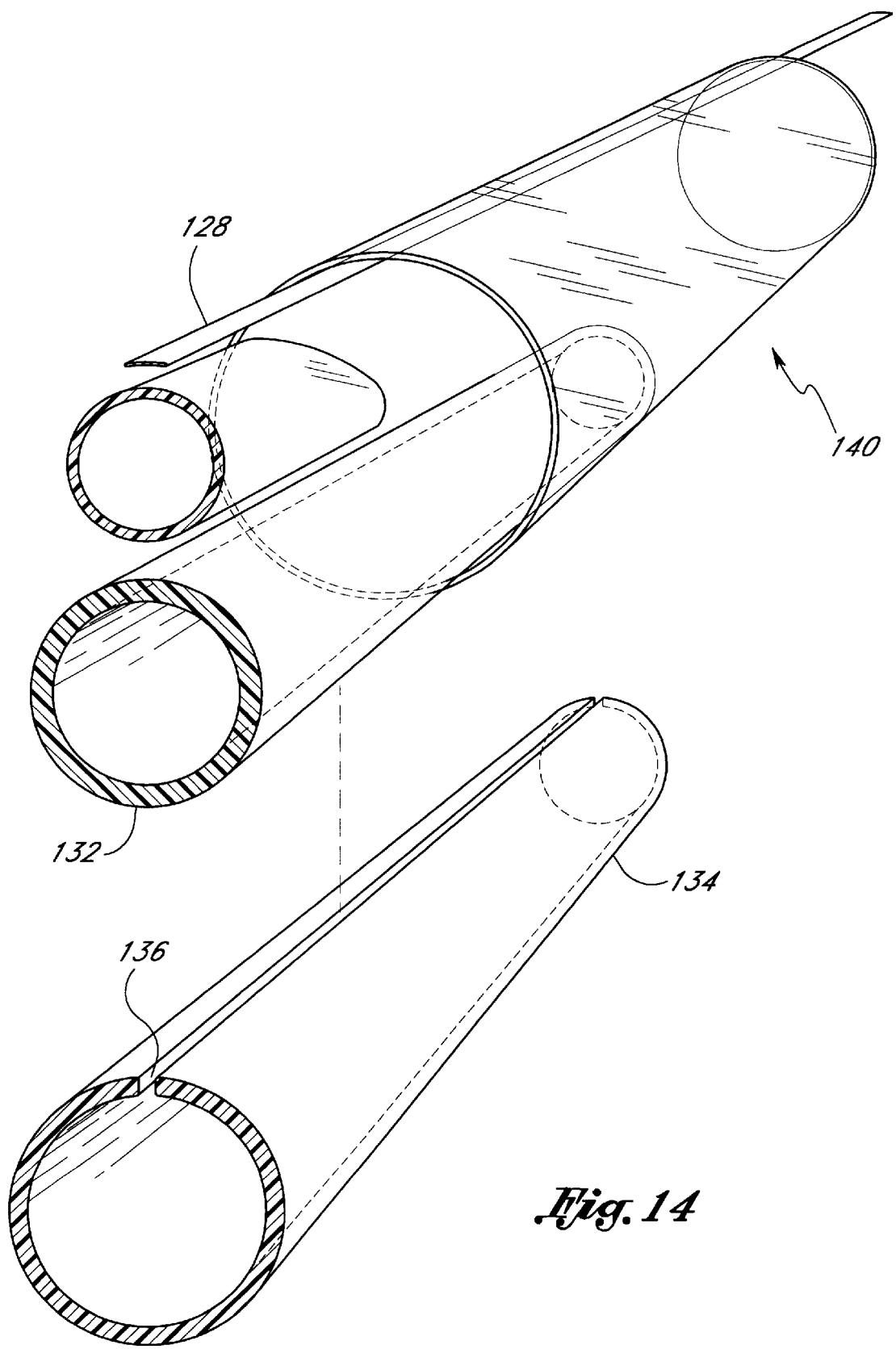
FIG. 14 is an exploded view of the present access device illustrating the method of its construction.

FIG. 14 is an exploded view of the present access device, illustrating a method of construction of the guide channel 120. Preferably, the main tubing 132 is preformed into the desired configuration, including any curvature. The guide channel membrane 140, which may take the form of an extruded tubing, as illustrated in FIG. 14, or other configuration, is then placed eccentrically around the main tubing 132. The nylon split sheath 134 is then mechanically expanded so as to surround the main tubing/membrane material, thereby capturing the membrane 140 around the tubing 132. During this process the excess membrane material is allowed to protrude through the slit or neck 136 in the split sheath 134 and is then folded or stored with respect to the access device 100 in accordance with various configurations discussed above. Covers or forms are placed onto the folded membranes and closely conform to the profile of the introducer 100. These elements keep the membrane 140 in close configuration prior to heat setting.

It will be noted from FIG. 14 that the reinforcement device is inserted within the guide channel membrane prior to its capture by the split sheath. To facilitate instrument insertion, the reinforcement device extends proximally along the merge channel so that the instrument rides below it as the instrument emerges from the distal end of the merge channel and begins to deploy the guide channel.

Another method of forming a closely fitting mold is to swell an elastomeric tubing, such as silicone, with Freon. Prior to swelling, the silicone tubing is of a smaller diameter than the introducer 100. Once swollen and enlarged, the silicone tubing is slid over the folded membrane and introducer. When the Freon evaporates, the silicone tubing will resume its pre-enlarged state thereby creating a tightly fitting mold over the membrane. After heat setting, the silicone tubing can be removed from the introducer leaving the membrane in a tight configuration with the introducer. In any case, a moderate amount of heat is applied to the access device in order to thermoplastically set the guide channel membrane in its stored position. In one preferred embodiment, the PET material which comprises the guide channel membrane has a glass transition temperature of 180° F. Thus, the setting temperature used in this method of construction is preferably about 160° F. It will be noted in this regard that sterilization of the system is achieved at about 140° F.

The present method is not limited to that illustrated in FIG. 14 or described above. A number of other methods of construction will become apparent to those of ordinary skill. For example, because of the thermoplastic nature of the membrane material, heat forming or heat shrinking can easily be employed in other aspects of the construction method. Although most costly, adhesives or other mechanical fasteners can be utilized. Some adhesive systems can be effectively incorporated into the design of the membrane material, main tube or slit sheath by making these tubes as a co-extrusion with a secondary bonding material as a composite within the tubing material or body in which thermal bonding techniques can be employed. Heat-activated or hot-melt adhesives, UV cured adhesives, or pressure-sensitive adhesive systems can also be used to facilitate attachment of the membrane channel or for keeping the folded membrane tacked down onto the surface of the main tube.

In conclusion, the laparoscopic introducer of the present invention, including its method of use and construction, represents a marked advancement in the art of laparoscopic procedures. Thus, it should be understood that the scope of the present invention is not to be limited by the illustrations or foregoing description thereof, but rather by the appended claims, and certain variations and medications of this invention will suggest themselves to one of ordinary skill in the art.

What is claimed is:

1. A method of minimizing access trauma while percutaneously accessing an internal site in a patient for conducting an endoscopic procedure, comprising the steps of:

providing an access device having a proximal end, a distal end and an elongate body extending therebetween, said device comprising a first lumen and at least one second lumen defined at least in part by a substantially inelastic flexible wall, said second lumen having an internal cross-sectional area that is enlargeable from a first, reduced area to a second, enlarged area, said wall comprising a membrane initially self-retained in a configuration having said first, reduced cross-sectional area;

percutaneously advancing the access device into the patient while the second lumen is in the first, reduced cross-sectional area configuration;

enlarging the second lumen from the first, reduced cross-sectional area to the second enlarged cross-sectional area to provide percutaneous access to a working cavity in the patient by way of said second lumen; and introducing an instrument into the cavity by way of the second lumen to perform the endoscopic procedure.

2. A method as in claim 1, wherein said percutaneously advancing step is preceded by the additional steps of identifying an access site on the patient, and making an incision at the access site for receiving the access device.

3. A method of minimizing access trauma while percutaneously accessing an internal site in a patient for conducting an endoscopic procedure, comprising the steps of:

providing an access device having a proximal end, a distal end and an elongate body extending therebetween, said device comprising a first lumen having a substantially fixed interior cross-sectional area and at least one second lumen defined at least in part by a substantially inelastic flexible wall, said second lumen having an internal cross-sectional area that is enlargeable from a first, reduced area to a second, enlarged area, said wall initially self-retained so that the internal cross-sectional area is said first, reduced area;

percutaneously advancing the access device into the patient while the second lumen is in the first, reduced cross sectional area configuration;

enlarging the diameter of the second lumen from the first, reduced cross-sectional area to the second enlarged cross-sectional area to provide percutaneous access to a working cavity in the patient by way of said second lumen, said enlarging step comprising:

providing an elongate dilator having a tapered distal tip;

introducing the distal tip into the proximal end of the second lumen; and advancing the dilator distally through the second lumen; and introducing an instrument into the cavity by way of the second lumen to perform the endoscopic procedure.

4. A method as in claim 3, further comprising the step of removing the dilator prior to introducing the instrument by way of the second lumen.

5. A method as in claim 3, wherein the dilator comprises an elongate tubular wall having an axially extending working channel, and wherein the step of introducing the instrument comprises introducing the instrument through the working channel in the dilator.

6. A method as in claim 1, wherein the instrument comprises an elongate body having a functional distal tip, further comprising the step of diffusing the force of the distal tip of the instrument at the point of contact between the distal tip of the instrument and the wall of the second lumen.

7. A method of minimizing access trauma while percutaneously accessing an internal site in a patient for conducting an endoscopic procedure, comprising the steps of:

providing an access device having a proximal end, a distal end and an elongate body extending therebetween, said device comprising a first lumen having a substantially fixed interior cross-sectional area and at least one second lumen defined at least in part by a flexible wall, said second lumen having an internal cross-sectional area that is enlargeable from a first, reduced area to a second, enlarged area;

percutaneously advancing the access device into the patient while the second lumen is in the first, reduced cross sectional area configuration;

enlarging the diameter of the second lumen from the first, reduced cross-sectional area to the second enlarged cross-sectional area to provide percutaneous access to a working cavity in the patient by way of said second lumen;

introducing an instrument into the cavity by way of the second lumen to perform an endoscopic procedure, said instrument comprising an elongate body having a functional distal tip; and diffusing the force of the distal tip of the instrument at the point of contact between the distal tip of the instrument and the wall of the second lumen, said diffusing step being accomplished by providing an elongate force diffusing element extending axially along the wall of the second lumen, wherein the force diffusing element is not coextensive with the wall of the second lumen.

8. A method as in claim 7, wherein said diffusing step comprises providing an elongate metal ribbon extending axially along the wall of the second lumen.

9. A method of conducting an endoscopic procedure, comprising the steps of:

providing an elongate rigid walled introducer having an elongate tubular body with at least a first lumen extending axially therethrough and defined within a substantially rigid wall, said wall defining said first lumen and having a radially inwardly facing surface and a radially outwardly facing surface, the introducer also having at least a second lumen extending along the body parallel to the first lumen, said second lumen comprising a wall which is collapsible against the outwardly facing surface of the wall defining the first lumen;

introducing the introducer percutaneously into the patient;

expanding the collapsible wall to restore patency to the second lumen; and advancing an endoscopic tool in a distal direction transluminally through the second lumen along a longitudinal ribbon which guides the tool through said second lumen.

10. A method as in claim 9, further comprising the step of insufflating the patient by introducing an insufflation media through the elongate rigid walled introducer.

11. A method as in claim 10, further comprising the step of introducing an endoscope through the first lumen for visualizing a laparoscopic procedure surgical site.

12. A method for performing an endoscopic surgical procedure such as laparoscopy, comprising the steps of:

forming an endoscopic port so as to provide access to a bodily cavity;

providing a surgical access device for insertion through said port and into said bodily cavity, said surgical access device having a first channel in an open position and a second channel in a substantially closed position, the second channel being defined at least in part by an inelastic membrane which is folded and initially self-retained in the closed position so as not to substantially increase the cross-sectional profile of the access device;

inserting an endoscope through said first channel in order to visualize said bodily cavity; and unfolding the membrane to dilate said second channel so as to provide auxiliary access to said bodily cavity, by inserting an instrument into said second channel to perform said endoscopic procedure.

13. A method as in claim 1, further comprising the step of introducing an insufflation media through the first lumen to enlarge the cavity in the patient.

14. A method as in claim 12, further comprising the step of providing distension media through said first channel.

15. A method of percutaneously accessing an internal site in a patient for conducting an endoscopic procedure, comprising the steps of:

providing an access device having a proximal end, a distal end and an elongate body extending therebetween, said device comprising a first lumen and at least one second lumen defined at least in part by a substantially inelastic flexible wall, said second lumen having an internal cross-sectional area that is enlargeable from a first, reduced area to a second, enlarged area;

percutaneously advancing the access device into the patient while the second lumen is in the first, reduced cross-sectional area configuration;

enlarging the internal cross-sectional area of the second lumen from the first, reduced cross-sectional area to the second enlarged cross-sectional area to provide percutaneous access to a working cavity in the patient by way of said second lumen;

advancing distally through the second lumen an elongate instrument having a distal tip, said advancing including guiding the instrument along a reinforcing rib within the second lumen to facilitate insertion of the instrument through the second lumen; and introducing the instrument into the cavity by way of the second lumen to perform the endoscopic procedure.

16. The method as in claim 15, further comprising diffusing the force of the distal tip of the instrument at the point of contact between the distal tip of the instrument and the wall of the second lumen, said diffusing accomplished by providing an elongate force diffusing element extending axially along the wall of the second lumen.

17. The method as in claim 15, wherein the instrument comprises an elongate body having a functional distal tip which is bevelled along only one side, further comprising the step of diffusing the force of the distal tip of the instrument at the point of contact between the distal tip of the instrument and the wall of the second lumen.

18. The method as in claim 17, wherein said diffusing step is accomplished by providing an elongate force diffusing element extending axially along the wall of the second lumen.

19. The method as in claim 15, further comprising providing a reinforcement device for guiding the instrument into a specific location within the patient's body.

20. A surgical access device having a proximal end, a distal end and an elongate body extending therebetween, said device comprising:

a first lumen having a substantially fixed interior cross-sectional area;

at least one second lumen for the insertion of an instrument, said second lumen defined at least in part by a substantially flexible wall and having an internal cross-sectional area that is enlargeable from a first, reduced area to a second, enlarged area; and a reinforcing device positioned longitudinally within said second lumen to guide the instrument through said second lumen.

21. A surgical access device having a proximal end, a distal end and an elongate body extending therebetween, said device comprising:

a first lumen having a substantially fixed interior cross-sectional area;

at least one second lumen for the insertion of an instrument, said second lumen defined at least in part by a substantially flexible wall and having an internal cross-sectional area that is enlargeable from a first, reduced area to a second, enlarged area; and a reinforcing device within said second lumen to facilitate insertion of the instrument through said second lumen, wherein said reinforcing device is a flat wire.

22. The surgical access device of claim 21, wherein the thickness of said reinforcing device is between 0.001 inches to 0.004 inches.

23. The surgical access device of claim 21, wherein said reinforcing device is made of stainless steel.

24. The surgical access device of claim 20, wherein said reinforcing device comprises lateral walls to guide the instrument through said second lumen.

25. The method of claim 1, wherein the said step of enlarging the diameter of the second lumen is performed by inserting a dilator through said second lumen.

26. The method of claim 25, wherein said dilator has a distal tip which is bevelled along only one side.

27. The method as in claim 2, wherein said step of making an incision is accomplished by introducing a Veress needle through said first lumen and advancing the access device, with the Veress needle in said first lumen, into the patient's body.

28. The method as in claim 27, further comprising the steps of withdrawing the Veress needle from the first lumen and introducing a laparoscope into the first lumen of the access device.

29. The method as in claim 28, wherein said enlarging step is performed while the laparoscope is within the first lumen.

30. A method of minimizing access trauma while percutaneously accessing an internal site in a patient for conducting a laparoscopic procedure, comprising the steps of:

providing an access device having a proximal end, a distal end and an elongate body extending therebetween, said device comprising a first lumen having a substantially fixed interior cross-sectional area and at least one second lumen defined at least in part by a substantially inelastic flexible wall, said second lumen having an internal cross-sectional area that is enlargeable from a first, reduced area to a second, enlarged area;

percutaneously advancing the access device into the patient while the second lumen is in the first, reduced cross sectional area configuration;

enlarging the diameter of the second lumen from the first, reduced cross-sectional area to the second enlarged cross-sectional area to provide percutaneous access to a working cavity in the patient by way of said second lumen;

introducing an instrument into the cavity by way of the second lumen to perform a laparoscopic procedure, said instrument comprising an elongate body having a functional distal tip; and diffusing the force of the distal tip of the instrument at the point of contact between the distal tip of the instrument and the wall of the second lumen, wherein said diffusing step comprises providing an elongate metal ribbon extending axially along the wall of the second lumen.

* * * * *